(12) United States Patent
Cowan

(10) Patent No.: US 10,543,312 B2
(45) Date of Patent: Jan. 28, 2020

(54) FLUID DELIVERY SYSTEM AND METHOD OF FLUID DELIVERY TO A PATIENT

(71) Applicant: BAYER HEALTHCARE LLC, Whippany, NJ (US)

(72) Inventor: Kevin P. Cowan, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 15/274,411

(22) Filed: Sep. 23, 2016

(65) Prior Publication Data
US 2017/0014568 A1 Jan. 19, 2017

Related U.S. Application Data

(62) Division of application No. 13/826,483, filed on Mar. 14, 2013, now Pat. No. 9,486,573.

(51) Int. Cl.
*A61M 5/14* (2006.01)
*A61M 5/145* (2006.01)
(Continued)

(52) U.S. Cl.
CPC .......... *A61M 5/1409* (2013.01); *A61B 5/055* (2013.01); *A61B 6/032* (2013.01); *A61B 6/481* (2013.01);
(Continued)

(58) Field of Classification Search
CPC .............. A61M 5/1407; A61M 5/1408; A61M 5/1409; A61M 5/16827; A61M 5/007;
(Continued)

(56) References Cited

U.S. PATENT DOCUMENTS

| 1,367,008 A | 2/1921 | Bessese |
| 4,006,736 A | 2/1977 | Kranys et al. |

(Continued)

FOREIGN PATENT DOCUMENTS

| EP | 0945150 A2 | 9/1999 |
| JP | H0377070 A | 4/1991 |

(Continued)

OTHER PUBLICATIONS

"Extended European Search Report from EP Application No. 14825990", dated Mar. 2, 2017.
(Continued)

*Primary Examiner* — Nilay J Shah
(74) *Attorney, Agent, or Firm* — James R. Stevenson; Ryan Miller

(57) ABSTRACT

A fluid delivery system includes a pressurizing mechanism. The pressurizing mechanism includes: a substantially cylindrical body having a movable member positioned therein that divides the body into a first chamber and a second chamber; a plunger rod connected to a first side of the movable member and extending through a substantially closed first end of the body; and an elongated member connected to a second side of the movable member and extending through a substantially closed second end of the body. The plunger rod configured to operatively engage a fluid container. Fluid is dispensed from the fluid container by forming a vacuum within at least the first chamber by moving the movable member toward the second end of the body, allowing atmospheric pressure to enter the second chamber, and actuating the pressurizing mechanism to cause the moving member to move towards the first end of the body.

6 Claims, 18 Drawing Sheets

(51) Int. Cl.
  *A61M 5/00* (2006.01)
  *A61M 5/20* (2006.01)
  *A61B 5/055* (2006.01)
  *A61B 6/03* (2006.01)
  *A61B 6/00* (2006.01)
  *A61M 39/24* (2006.01)
  *A61M 5/315* (2006.01)

(52) U.S. Cl.
  CPC ............ *A61B 6/504* (2013.01); *A61M 5/007* (2013.01); *A61M 5/14526* (2013.01); *A61M 5/2053* (2013.01); *A61M 39/24* (2013.01); *A61M 5/1452* (2013.01); *A61M 5/14546* (2013.01); *A61M 5/14566* (2013.01); *A61M 5/31568* (2013.01); *A61M 2005/1403* (2013.01); *A61M 2005/14513* (2013.01); *A61M 2205/3306* (2013.01); *A61M 2205/3317* (2013.01); *A61M 2205/3375* (2013.01)

(58) Field of Classification Search
  CPC ............ A61M 5/14526; A61M 5/2053; A61M 5/1452; A61M 2005/1403
  See application file for complete search history.

(56) References Cited

U.S. PATENT DOCUMENTS

| | | | |
|---|---|---|---|
| 4,323,066 | A | 4/1982 | Bourdon |
| 4,367,737 | A | 1/1983 | Kozam et al. |
| 4,677,980 | A | 7/1987 | Reilly et al. |
| 4,936,315 | A | 6/1990 | Lineback |
| 5,033,650 | A | 7/1991 | Colin et al. |
| 5,135,500 | A | 8/1992 | Zdeb |
| 5,176,642 | A | 1/1993 | Clement |
| 5,279,608 | A | 1/1994 | Cherif Cheikh |
| 5,312,389 | A | 5/1994 | Theeuwes et al. |
| 5,383,858 | A | 1/1995 | Reilly et al. |
| 5,494,036 | A | 2/1996 | Uber, III et al. |
| 5,553,619 | A | 9/1996 | Prince |
| 5,588,556 | A | 12/1996 | Sancoff et al. |
| 5,746,208 | A | 5/1998 | Prince |
| 5,769,824 | A | 6/1998 | Hjertman et al. |
| 5,827,262 | A | 10/1998 | Neftel et al. |
| 5,911,252 | A | 6/1999 | Cassel |
| RE37,602 | E | 3/2002 | Uber, III et al. |
| 6,387,228 | B1 | 5/2002 | Maget |
| 6,413,238 | B1 | 7/2002 | Maget |
| 6,425,885 | B1 | 7/2002 | Fischer et al. |
| 6,638,244 | B1 | 10/2003 | Reynolds |
| 6,656,157 | B1 | 12/2003 | Duchon et al. |
| 6,704,592 | B1 | 3/2004 | Reynolds et al. |
| 6,875,203 | B1 | 4/2005 | Fowles et al. |
| 6,923,800 | B2 | 8/2005 | Chen et al. |
| 7,115,117 | B2 | 10/2006 | Shiraishi et al. |
| 7,221,159 | B2 | 5/2007 | Griffiths et al. |
| 7,283,860 | B2 | 10/2007 | Frazier et al. |
| 7,315,109 | B1 | 1/2008 | Griffiths et al. |
| 7,407,490 | B2 | 8/2008 | Bendsen et al. |
| 7,632,245 | B1* | 12/2009 | Cowan ............ A61M 5/14526 600/420 |
| 7,736,353 | B2 | 6/2010 | Reynolds |
| 9,101,713 | B2 | 8/2015 | Cowan et al. |
| 2001/0056233 | A1 | 12/2001 | Uber et al. |
| 2002/0017484 | A1 | 2/2002 | Dourdeville |
| 2002/0107481 | A1 | 8/2002 | Reilly et al. |
| 2002/0115933 | A1 | 8/2002 | Duchon et al. |
| 2002/0165490 | A1 | 11/2002 | Minezaki et al. |
| 2003/0176833 | A1 | 9/2003 | Libermann |
| 2003/0199787 | A1 | 10/2003 | Schwindt |
| 2003/0236442 | A1 | 12/2003 | Connors et al. |
| 2004/0030233 | A1 | 2/2004 | Frazier et al. |
| 2004/0171983 | A1 | 9/2004 | Sparks et al. |
| 2004/0181147 | A1 | 9/2004 | Prince |
| 2004/0193045 | A1 | 9/2004 | Scarborough et al. |
| 2005/0070848 | A1 | 3/2005 | Kim et al. |
| 2005/0084395 | A1 | 4/2005 | Kang |
| 2005/0107738 | A1 | 5/2005 | Slater et al. |
| 2005/0197531 | A1 | 9/2005 | Cabiri et al. |
| 2005/0209790 | A1 | 9/2005 | Niethammer |
| 2007/0043319 | A1 | 2/2007 | Kimmel et al. |
| 2008/0097389 | A1* | 4/2008 | Wilson ............... A61M 1/0281 604/518 |
| 2008/0167621 | A1* | 7/2008 | Wagner .................. A61M 5/19 604/191 |
| 2010/0305507 | A1 | 12/2010 | Duncan |
| 2011/0282197 | A1 | 11/2011 | Martz |
| 2012/0323173 | A1 | 12/2012 | Thorne, Jr. et al. |
| 2013/0172818 | A1 | 7/2013 | Schraga |

FOREIGN PATENT DOCUMENTS

| | | |
|---|---|---|
| JP | A04221567 | 8/1992 |
| JP | H0520751 U | 3/1993 |
| JP | H05345024 A | 12/1993 |
| JP | U06070738 | 10/1994 |
| JP | H08511460 A | 12/1996 |
| JP | H11276581 A | 10/1999 |
| JP | 2002035125 A | 2/2002 |
| JP | 2008149119 A | 7/2008 |
| JP | 2011528574 A | 11/2011 |
| WO | 9004987 A1 | 5/1990 |
| WO | 9106338 A1 | 5/1991 |
| WO | 9201484 A1 | 2/1992 |
| WO | 9528977 A1 | 11/1995 |
| WO | 0100261 A1 | 1/2001 |
| WO | 0192907 A2 | 12/2001 |

OTHER PUBLICATIONS

"Supplementary European Search Report from EP Application No. EP14825990", dated Feb. 20, 2017.

"Supplementary European Search Report from EP Application No. EP14774466", dated Oct. 5, 2016.

International Preliminary Report on Patentability dated Sep. 24, 2015 from corresponding PCT Application No. PCT/US2014/023214.

International Search Report and Written Opinion dated Jun. 10, 2014 from corresponding PCT Application No. PCT/US2014/020260.

International Search Report and Written Opinion dated Jul. 8, 2014 of corresponding PCT Application No. PCT/US2014/023214.

Written Opinion and International Search Report dated Feb. 10, 2015 from related PCT Application No. PCT/US2014/046618.

"A Primer on Medical Device Interactions with magnetic Resonance Imaging Systems," accessed at http://www.fda.gov/cdrh/ode/primerf6.html, accessed on Sep. 5, 2007, pp. 15.

"A Primer on Medical Device Interactions With Magnetic Resonance Imaging Systems," U. S. Food and Drug Administration, Center for Devices and Radiological Health (Feb. 7, 1997).

International Preliminary Report on Patentability and Written Opinion dated Sep. 24, 2015 from PCT Application No. PCT/US2014/020260; 7 pages.

"International Preliminary Report on Patentability dated Jan. 28, 2016 from PCT/US2014/046618".

Keeler, E.K., et al., "Accessory Equipment Considerations with Respect to MRI Compatibility," JMRI, vol. 8, No. 1, pp. 12-18 (1998).

Lemieux, L, et al. "Recording of EEG during fMRI experiments: patient safety," Magnetic Resonance in Medicine, vol. 38, No. 6, pp. 943-952, John Wiley & Sons, Inc. (1997).

U.S. Appl. No. 10/916,946, filed Aug. 12, 2004, Griffiths et al.

"Supplementary European Search Report from EP Application No. EP14779557", dated Oct. 25, 2016.

* cited by examiner

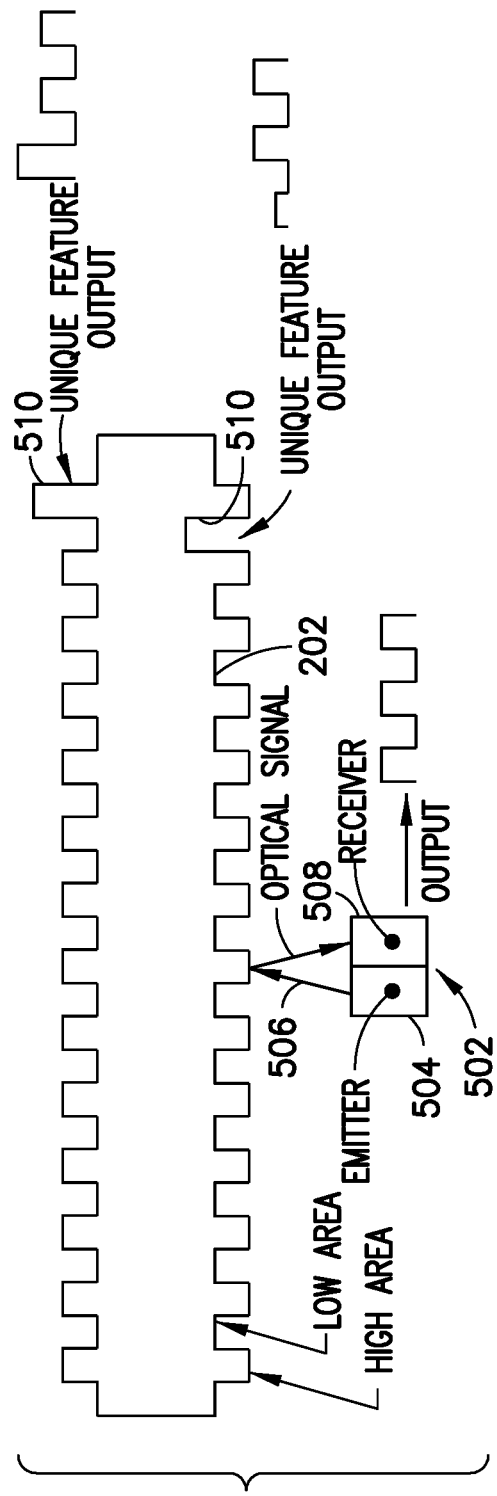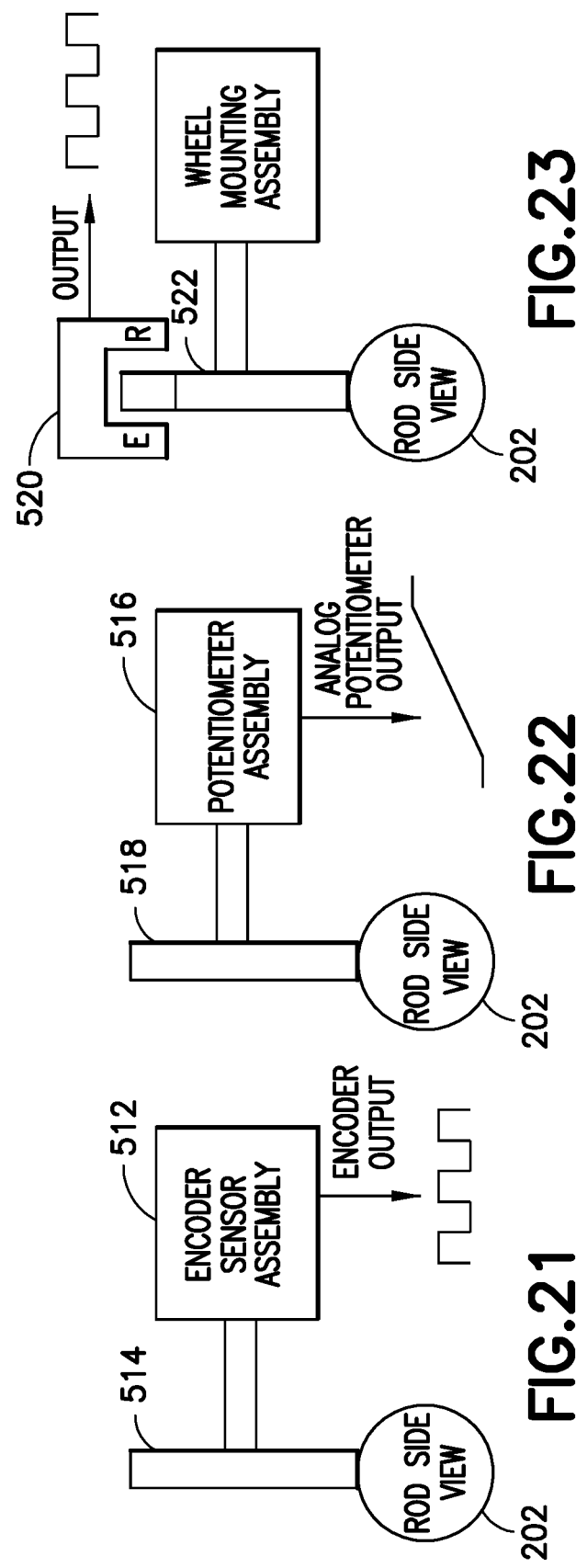

FLUID DELIVERY SYSTEM AND METHOD OF FLUID DELIVERY TO A PATIENT

CROSS-REFERENCE TO RELATED APPLICATION

This application is a divisional of U.S. patent application Ser. No. 13/826,483 filed 14 Mar. 2013, the disclosure of which incorporated herein by reference and assigned to the assignee of the invention disclosed below.

BACKGROUND OF THE INVENTION

Field of the Invention

The present invention relates generally to devices, systems and methods for delivery of a fluid, and, particularly, for infusion or injection of a fluid into a patient.

Description of Related Art

A number of injector-actuated syringes and powered injectors for use in medical procedures such as angiography, computed tomography (CT), ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

Although significant advances have been made in the design and operation of powered injectors, a number of problems persist which can limit their use. For example, each year in the United States several million MRI procedures are performed. However, powered injectors are used in only a relatively small percentage of such procedures. In MRI procedures in which there is no need to accurately control the timing of contrast injection or the flow rate of injection, powered injectors are almost never used. In that regard, MRI procedures are relatively expensive and patient throughput is a primary concern. It is perceived that use of powered injectors in such procedures will require additional time, while providing little benefit. Thus, in contrast-enhanced procedure in which timing and flow rate control are not important, contrast is currently injected manually. Typically, the patient is placed in the MRI bore and a baseline scan is performed. The patient is then removed from the bore of the imaging device and the contrast is injected. The patient is then once again placed in the bore and the contrast-enhanced imaging is performed.

A number of problems often arise with the manual injection of contrast in an MRI procedure. For example, after injection it is often difficult to reposition the patient in the same position in which the baseline measurement was made. Even if repositioning can be achieved with success, removal of the patient from the bore to manually inject contrast and subsequent repositioning require a substantial amount of time. Moreover, in some instances, particularly with claustrophobic patients, the patient refuses to reenter the bore. Furthermore, it is sometimes difficult with some patients to properly inject the contrast manually. In such cases, it may become necessary to call for the services of an IV specialist team, greatly increasing the amount of time required for the scan.

Even in imaging procedures other than MRI procedures (such as CT, angiography, and ultrasound), there may be reluctance to use powered injectors in certain procedures because of perceived or actual burdens with such use.

For the above reasons and others, it is desirable to develop improved devices, systems, and methods for the injection of fluids into patients.

SUMMARY OF THE INVENTION

An object of the invention described hereinafter is to provide an injection device that is readily fabricated to be fully in-bore compatible for MR procedures. A further object is to provide an injection device that can, for example, be applied to a patient outside the scanning room such that there is no need to remove a patient from the scanner bore to perform an injection. An additional object is to keep the time required for set up of the devices described hereinafter minimal. Yet another objective is to provide injection devices that are readily adaptable for remote activation, for example, from a scan control room.

According to one aspect of the invention, provided is a fluid delivery system that includes a pressurizing mechanism. The pressurizing mechanism includes: a substantially cylindrical body having a movable member positioned therein that divides the body into a first chamber and a second chamber; a plunger rod connected to a first side of the movable member and extending through a substantially closed first end of the body; and an elongated member connected to a second side of the movable member and extending through a substantially closed second end of the body. The plunger rod configured to operatively engage a fluid container. Fluid is dispensed from the fluid container by forming a vacuum within at least the first chamber by moving the movable member toward the second end of the body, allowing atmospheric pressure to enter the second chamber, and actuating the pressurizing mechanism to cause the moving member to move towards the first end of the body and forcing the plunger rod to move within the fluid container.

The fluid container may be a syringe that includes: a substantially cylindrical syringe barrel having a fluid dispensing end and an open end; and a plunger configured to be received within the open end of the syringe barrel. The plunger rod is configured to operatively engage the plunger when the syringe is connected to the first end of the body. A valve may be in fluid communication with the second chamber. The movement of the movable member toward the second end of the body may cause air to be expelled from the second chamber through the valve, and atmospheric pressure is allowed to enter the second chamber by opening the valve.

The movable member may include a seal that isolates the first chamber from the second chamber. A disposable fluid set may be connected between the fluid dispensing end of the fluid container and a patient. The disposable fluid set may require less than three inches of connective tubing. Desirably, no more than one foot of connective tubing is required between the injection devices of the present invention and the injection point on the patient. Given the proximity of placement of the fluid delivery system to the patient, no saline flush to remove expensive contrast medium from the fluid path is required as is often necessary with current powered injectors in which long lengths of connective tubing are required.

The fluid delivery system may further include an actuator connected to a fluid dispensing end of the fluid container. The actuator is switchable between a first state in which fluid is prevented from flowing through the fluid dispensing end and a second state in which the fluid can flow through the fluid dispensing end. The pressurizing mechanism may be actuated by switching the actuator from the first state to the second state. The actuator may be positioned within the disposable fluid set. A mechanism of the actuator may be selected from a rotary valve, a pinch valve with tubing, a ratchet valve, a fusible link, a trumpet valve, a port closing valve, a pump system, or a drive system. The mechanism of the actuator may be powered by a vacuum drive, a piezoelectric drive, an electric motor drive, a solenoid drive, an electro-resistive pump, a charged ion pump, a magneto restrictive material, a TCAM device, a shape memory alloy material, a state transition, a bi-metallic material, an electroactive polymeric material, pneumatic or hydraulic pressure, or gravity.

The fluid delivery system may further include a controller configured to control the state of the actuator. The controller may be remote from the actuator. The controller may control the state of the actuator via ultrasound, via a protocol of an imaging scanner, via microwave energy, via a mechanical link, via infrared light, via fiber optic cable, via pneumatic power, via hydraulic power, via voice activation, via movement of a scanner table, via time delay, via an RF gradient trigger from a scanner, via a photo cell, via optical light, via an RF signal, or via line power.

The syringe, the pressurizing mechanism, and the actuator may be configured to be MR compatible, thereby making the system suitable for use in or near the bore of an MR scanner.

In one embodiment of the invention, the elongated member may be a rod having a first end connected to the second side of the movable member and a second end extending through the substantially closed second end of the body. The second end of the rod may include a handle, thereby allowing a user to manually move the movable member toward the second end of the body.

In another embodiment, the elongated member may be a threaded rod having a first end connected to the second side of the movable member and a second end extending through the substantially closed second end of the body. In such an embodiment, the fluid delivery system may further include a releasable nut positioned at the second end of the body. The releasable nut may be configured to secure the threaded rod when in a closed position and release the threaded rod when in a released position. A lever may be provided that extends from the second end of the body for moving the nut from the closed position to the released position. The threaded rod may be rotated to move the moveable member toward the second end of the body with the nut in the closed position and the lever is moved to place the nut in the released position prior to switching the actuator.

While it has been described hereinabove that a saline flush is not required, in certain instances, it may be desirable to follow the injection of an injection fluid (for example, contrast medium, stress agents, saline, blood pool agents and/or organ specific agents) with an injection of saline. In such instances, the fluid delivery system may further include: a second pressurizing mechanism having a second substantially cylindrical body having a second movable member positioned therein that divides the second body into a first chamber and a second chamber; a second plunger rod connected to a first side of the second movable member and extending through a substantially closed first end of the second body; and a second elongated member connected to a second side of the second movable member and extending through a substantially closed second end of the second body. The second plunger rod is configured to operatively engage a second fluid container. A fluid path set desirably extends from a fluid dispensing end of the fluid container and a fluid dispensing end of the second fluid container to a patient.

In such an embodiment, a one-way check valve may be positioned within the fluid path set downstream from the fluid dispensing end of the second fluid container and upstream from the fluid dispensing end of the fluid container. A diameter of the fluid container is smaller than a diameter of the second fluid container such that a fluid within the fluid container is delivered at a higher pressure than a fluid in the second fluid container. Alternatively, a diameter of the substantially cylindrical body may be larger than a diameter of the second substantially cylindrical body such that a fluid within the fluid container is delivered at a higher pressure than a fluid in the second fluid container. A fluid (for example, contrast medium, stress agents, saline, blood pool agents and/or organ specific agents) within the fluid container may be different than a fluid (for example, saline) within the second fluid container.

In another embodiment of the infusion device being used to deliver a first fluid followed by a second fluid, a first one-way check valve may be positioned at the fluid dispensing end of the fluid container and a second one-way check valve may be positioned at the fluid dispensing end of the second fluid container. The second one-way check valve may have a crack pressure that is greater than a crack pressure of the first one-way check valve such that a fluid within the fluid container is delivered before a fluid in the second fluid container when the pressurizing mechanism and the second pressurizing mechanism are actuated. Alternatively, the fluid delivery system will work similarly if the first one-way check valve is removed.

Also provided is a fluid delivery system that includes: a pressurizing mechanism having a substantially cylindrical body having a substantially closed first end; a substantially closed second end; and a movable member positioned therein that divides the body into a first chamber and a second chamber; and an actuator connected to a fluid dispensing end of a fluid container, the actuator being switchable between a first state in which fluid is prevented from being delivered and a second state in which the fluid is dispensed. The fluid container is operatively coupled to the first end of the pressurizing mechanism. Fluid is dispensed from the fluid container by forming a vacuum within at least the first chamber by moving the movable member toward the second end of the body, allowing atmospheric pressure to enter the second chamber, and switching the actuator from the first state to the second state.

Further provided is a system for use in magnetic resonance (MR) imaging. The system includes an MR scanner defining a bore in which a patient is positioned for a scan; and a device for injection of at least one fluid into the patient. The device for injection includes: a syringe having a plunger slideably positioned therein and a fluid dispensing end; a pressurizing mechanism that includes a substantially cylindrical body having a substantially closed first end, a substantially closed second end, and a movable member positioned therein that divides the body into a first chamber and a second chamber; and an actuator connected to the fluid dispensing end of the syringe. The actuator is switchable between a first state in which fluid is prevented from flowing through the fluid dispensing end and a second state in which the fluid can flow through the fluid dispensing end. The syringe is operatively coupled to the first end of the pressurizing mechanism. The at least one fluid is dispensed by forming a vacuum within the first chamber and the second chamber by moving the movable member toward the second end of the body, opening the second chamber to atmospheric pressure, and switching the actuator from the first state to the second state.

According to yet another aspect of the invention, a fluid delivery system is provided that includes a first injection device, a second injection device, a fluid path set, an actuator, and a one-way check valve. The first injection device includes a first syringe configured to hold a first fluid and defining an outlet through which the first fluid can exit therefrom; and a first pressurizing mechanism comprising a first vacuum drive in operative connection with the plunger of the first syringe for pressurizing the fluid therein. The first syringe has a plunger slidably disposed therein and is configured to be placed in fluid connection with a patient. The second injection device includes a second syringe configured to hold a second fluid and defining an outlet through which the second fluid can exit therefrom; and a second pressurizing mechanism comprising a second vacuum drive in operative connection with the plunger of the second syringe for pressurizing the fluid therein. The second syringe has a plunger slidably disposed therein and is configured to be placed in fluid connection with the patient. The fluid path set extends from the outlet of the first syringe and the outlet of the second syringe to the patient. An actuator is connected to the outlet of the first syringe and the outlet of the second syringe. The actuator is switchable between a first state in which fluid is prevented from flowing through the outlet of the first syringe and the outlet of the second syringe and a second state in which fluid can flow through the outlet of the first syringe and the outlet of the second syringe. The one-way check valve is positioned within the fluid path set downstream from the outlet of the second syringe and upstream from the outlet of the first syringe. A diameter of the first syringe is smaller than a diameter of the second syringe such that the first fluid within the first syringe is delivered at a higher pressure than the second fluid in the second syringe and the one-way check valve prevents the first fluid from being delivered to the second syringe.

According to still another aspect of the invention, a fluid delivery system is provided that includes a first injection device, a second injection device, a fluid path set, an actuator, a first one-way check valve, and a second one-way check valve. The first injection device includes a first syringe configured to hold a first fluid and defining an outlet through which the first fluid can exit therefrom; and a first pressurizing mechanism comprising a first vacuum drive in operative connection with the plunger of the first syringe for pressurizing the fluid therein. The first syringe has a plunger slidably disposed therein and is configured to be placed in fluid connection with a patient. The second injection device includes a second syringe configured to hold a second fluid and defining an outlet through which the second fluid can exit therefrom; and a second pressurizing mechanism comprising a second vacuum drive in operative connection with the plunger of the second syringe for pressurizing the fluid therein. The second syringe has a plunger slidably disposed therein and is configured to be placed in fluid connection with the patient. The fluid path set extends from the outlet of the first syringe and the outlet of the second syringe to the patient. An actuator is connected to the outlet of the first syringe and the outlet of the second syringe. The actuator is switchable between a first state in which fluid is prevented from flowing through the outlet of the first syringe and the outlet of the second syringe and a second state in which fluid can flow through the outlet of the first syringe and the outlet of the second syringe. The first one-way check valve is positioned at the outlet of the first syringe and the second one-way check valve is positioned at the outlet of the second syringe. The second one-way check valve has a crack pressure that is greater than a crack pressure of the first one-way check valve such that, upon switching the actuator, the first fluid within the first syringe is delivered before the second fluid within the second syringe.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure. As used in the specification and the claims, the singular form of "a", "an", and "the" include plural referents unless the context clearly dictates otherwise.

BRIEF DESCRIPTION OF THE DRAWINGS

FIG. 20 is a schematic diagram of a first embodiment of a sensor assembly used to determine a position of the threaded rod of the pressurizing mechanism of FIG. 7;

FIG. 21 is a schematic diagram of a second embodiment of the sensor assembly used to determine a position of the threaded rod of the pressurizing mechanism of FIG. 7;

FIG. 22 is a schematic diagram of a third embodiment of the sensor assembly used to determine a position of the threaded rod of the pressurizing mechanism of FIG. 7; and FIG. 23 is a schematic diagram of a fourth embodiment of the sensor assembly used to determine a position of the threaded rod of the pressurizing mechanism of FIG. 7.

DETAILED DESCRIPTION OF THE PREFERRED EMBODIMENTS

Figure 1:
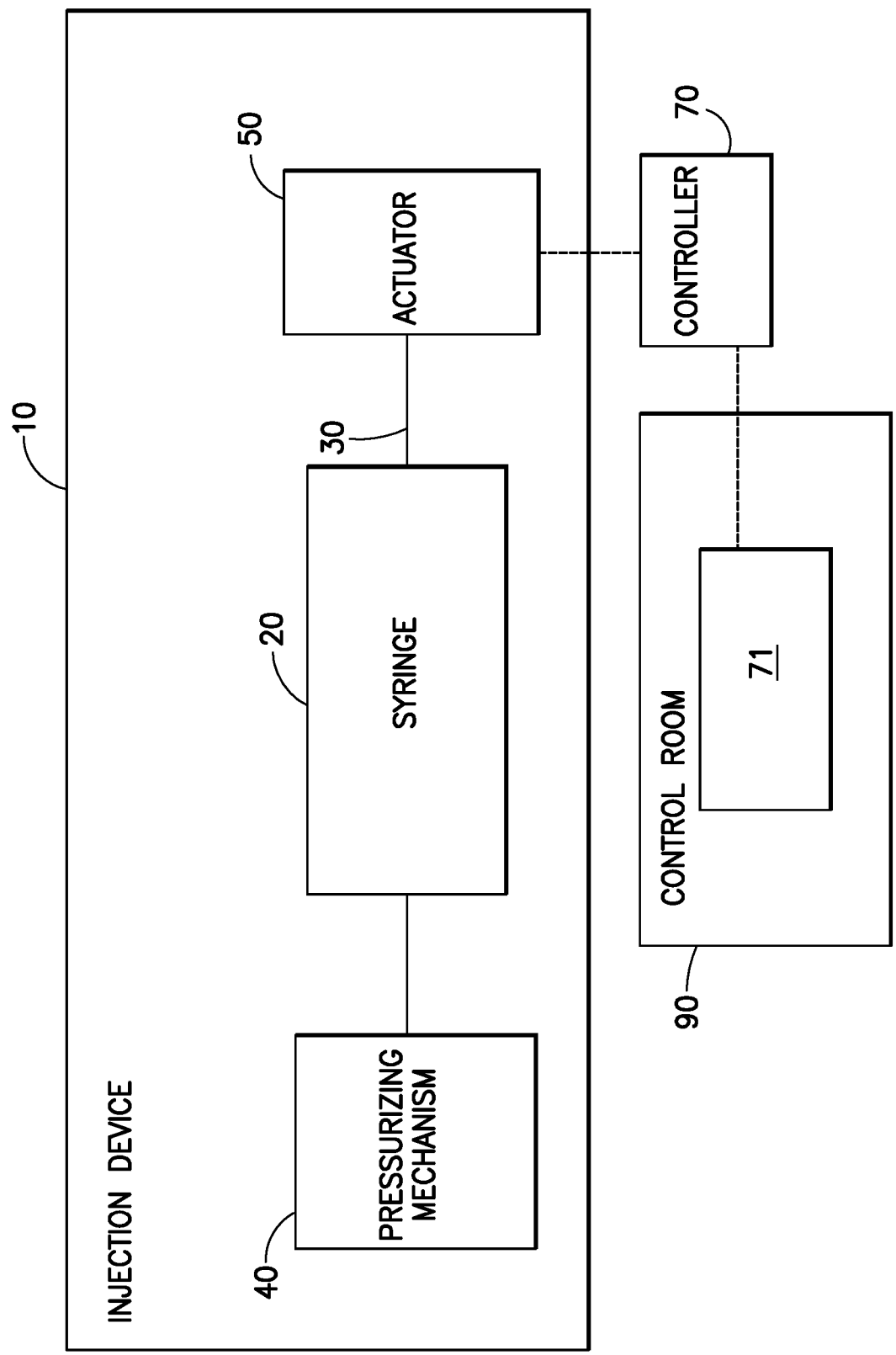
FIG. 1 is a schematic diagram of an injection or infusion device and system of the present invention.

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

In general, the present invention provides infusion or injection devices and systems that are relatively easy to operate. The injection device disclosed herein is related to the injection devices disclosed in U.S. Pat. No. 7,632,245, which is hereby incorporated by reference in its entirety.

In the embodiment of the present invention illustrated in FIG. 1, an injection or infusion device 10 includes a storage container or chamber 20 (for example, a prefilled syringe) in which a fluid for injection into a patient is stored. Injection device 10 includes an outlet 30 in fluid connection with chamber 20 and through which fluid exits chamber 20 to be injected into the patient. Injection device 10 also includes a pressurizing mechanism 40 through which force/pressure is applied to the fluid within chamber 20 to cause the pressurized fluid to exit outlet 30. Injection device 10 further includes an actuator 50 to initiate (and, possibly, terminate) flow. Actuator 50 can, for example, be operated by a controller 70 via a remote controller 71 from, for example, control room 90.

The pressurizing mechanism 40 can provide the force to pressurize the fluid in the container or chamber 20 via, for example, air displacement of a vacuum (a vacuum drive), a chemical reaction (for example, releasing an expanding gas), electrochemical reactions, electrical power (for example, from a battery, wall outlet, or from the scanner), expansion of a compressed gas (for example, $CO_2$ or air pressure); spring force, or gravity. The embodiments of the invention discussed hereinafter all utilize a vacuum drive pressurizing mechanism.

The actuator 50 can, for example, include a rotary valve at a syringe tip, a pinch valve with tubing, a ratchet valve, a fusible link, a trumpet valve, a port closing valve, a pump system, or a drive system to allow fluid to flow through outlet 30. The mechanism for operating the actuator 50 (or imparting motion thereto to change a state) can, for example, include a vacuum drive, a piezoelectric drive, an electric motor drive (for example, an inside-MRI bore air core motor in which the magnet of the bore forms part of the motor), a solenoid drive, an electric motor drive outside of the bore, an electro-resistive pump, a charged ion pump (available, for example, from Exigent), a magneto restrictive material (to which a voltage is applied), a thermochemical activated motion (TCAM) material or device, a nitinol material, a state transition (liquid to gas), a bi-metallic material (with different rates of expansion for each metal), an electro-active polymeric material, pneumatic or hydraulic pressure, and/or gravity. Power can be supplied via, for example, vacuum power, chemical power, electrical power (for example, battery power, wall outlet power), power from the scanner, human/manual power, compressed or pressurized gas (for example, $CO_2$ or air) power, hydraulic power, spring power, gravity power, or light/photoelectric power.

The controller 70 can, for example, control the state of the actuator 50 via ultrasound (for example, via a piezo tweeter operating through glass); via a scanner coil protocol (for example, GE/Siemens scanners comprise approximately 85% of the axial market and include two 15 volt connections); via microwave energy (for example, a glass smart link); via a mechanical or cable link (for example, via camera-type cable link using a plastic cable); via infrared light; via fiber optic cable; via pneumatic power; via hydraulic power; via patient operation; via voice activation; via movement of table 92; via time delay; via an RF gradient trigger from scanner (for example, 5th shim tune); via a photo cell; via optical light control; via line power (for example, via audio frequency through panel); via an RF link, or via operator manual control (that is, sending the operator into the MRI room to activate the device).

For use in an MR environment, the components of the injection device 10 are desirably fabricated from materials that are non-magnetic, non-ferrous, and/or otherwise suitable or compatible for use in an MRI environment. In general, many devices, including but not limited to many injectors and infusion pumps, that contain electric actuators such as DC brush motors, step motors, brushless DC motors or other wound coil motors and solenoids, often fail in a strong magnetic field as a result of damage to internal permanent magnets. Moreover, currents induced within the field windings of such devices from electromagnetic fields can cause overheating and potential damage to the windings and any connected electronic circuitry. The MRI magnetic field can also interfere with the device-created magnetic field and prevent accurate operation.

Furthermore, differences in magnetic permeability of materials within the actuator and eddy currents induced within actuator windings can affect the homogeneity or uniformity of the MRI magnetic field, generating image artifacts. Actuators that use mechanical commutation, such as DC brush motors, can also generate radio frequency energy during switching which can induce unwanted artifacts upon the acquired MRI images.

Figure 2:
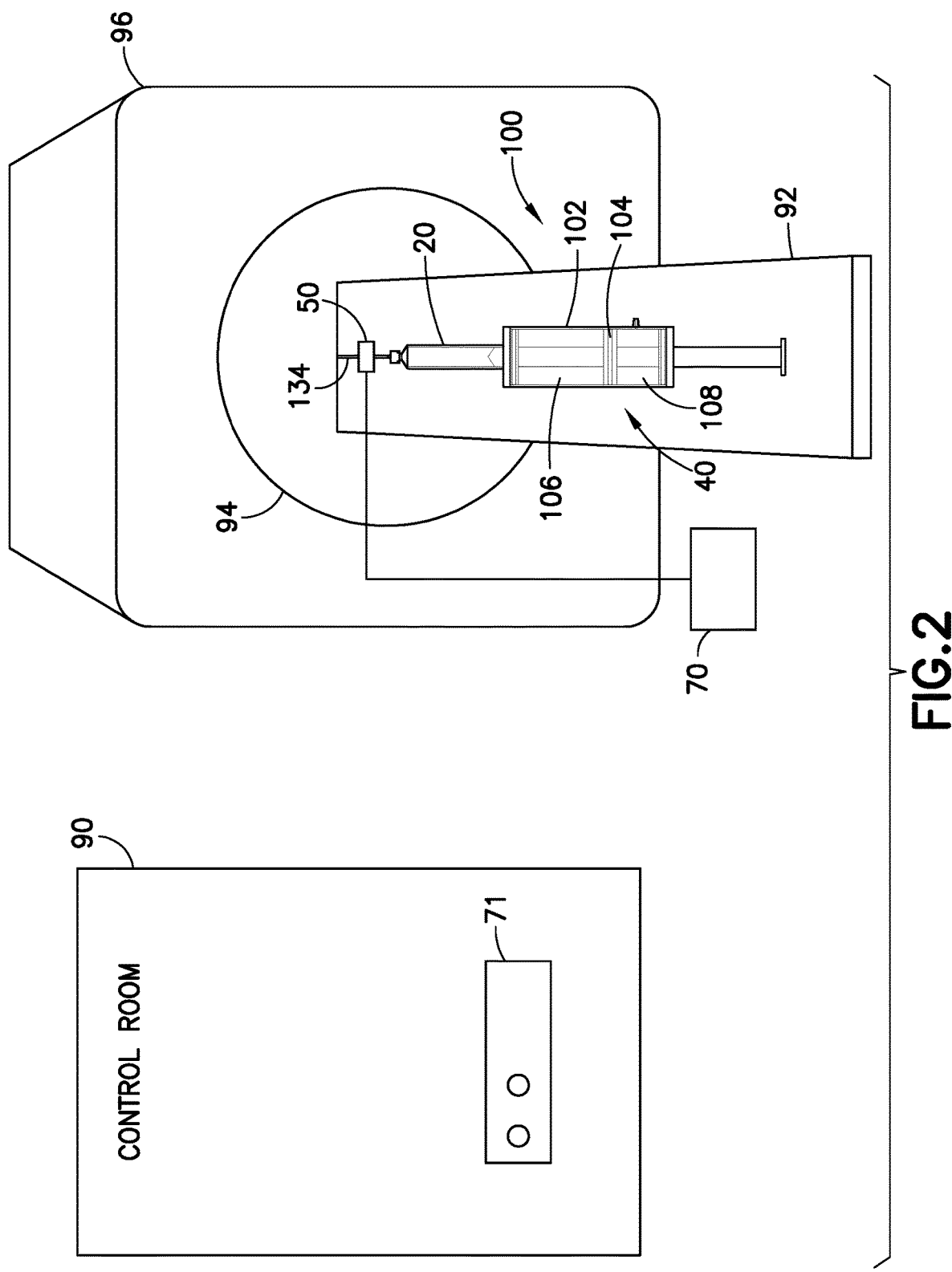
FIG. 2 illustrates one embodiment of an injection device and system of the present invention in an MR environment.

With reference to FIG. 2, one embodiment of an injection device 100 of the present invention can be used to inject fluid into the patient (not shown, but positioned on table 92 during an MRI procedure) within or within close proximity of the bore 94 of an MR Scanner 96.

Desirably, the injection devices of the present disclosure are suitable to be placed within one foot of the MRI bore. More desirably, the injection devices of the present disclosure are suitable to be placed within the bore, thereby providing close access to the injection site on the patient and eliminating lengthy connective tubing used with many currently available injection devices. In general, to be "MR compatible" as that phrase is used herein, the materials of injection device 100 should not interfere with the operation of the MR Scanner 96 in a substantial manner (for example, to cause image artifacts). Additionally, the MR environment (for example, the powerful magnetic field) should not substantially interfere with the operation of the injection device 100. Examples of suitable MRI compatible materials for the injection device 100 include, but are not limited to, polymeric materials, glass materials, and aluminum.

The container or chamber 20 for the injection fluid (generally an MR contrast fluid) can, for example, be a polymeric or glass MR syringe available, for example, from Medrad, Inc. of Indianola, Pa. Such syringes can be purchased "prefilled" with injection fluid or can be purchased empty and filled at the MRI site. The fluid in such syringes is pressurized via a plunger 25, which is slidably disposed within the syringe barrel.

Figure 3:
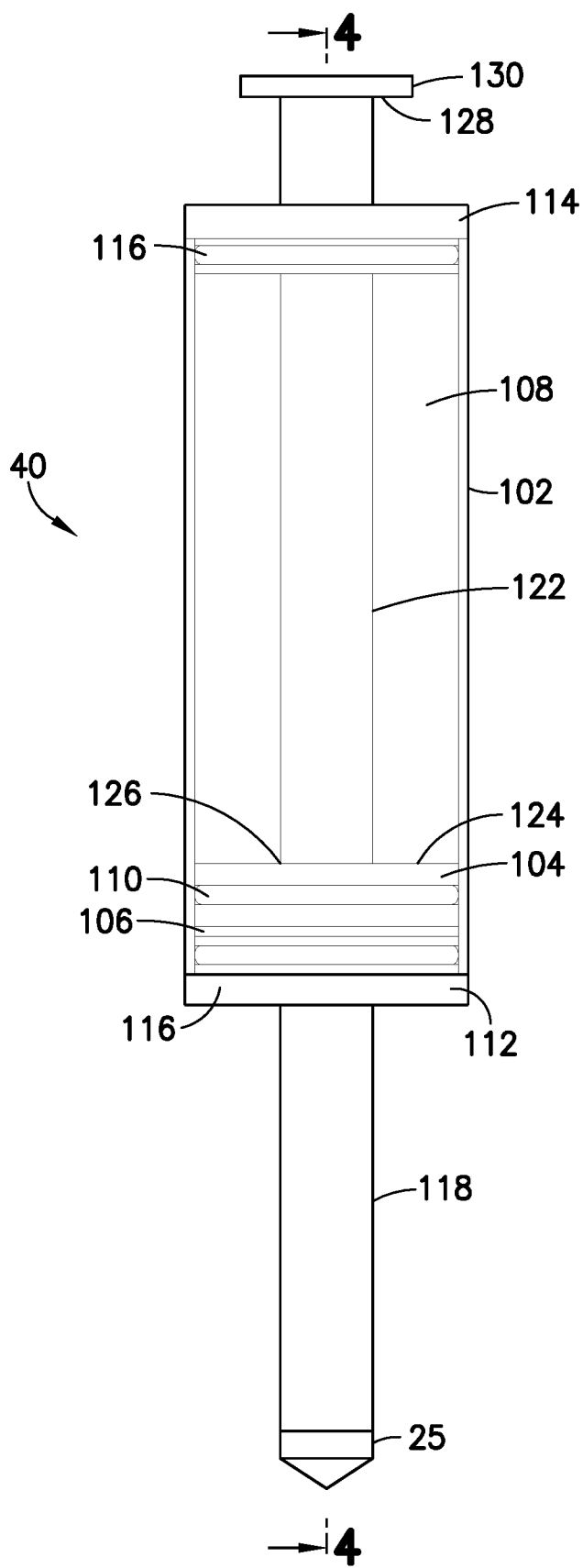
FIG. 3 is an enlarged side view of a pressurizing mechanism of the injection device of the system of FIG. 2.
Figure 4:
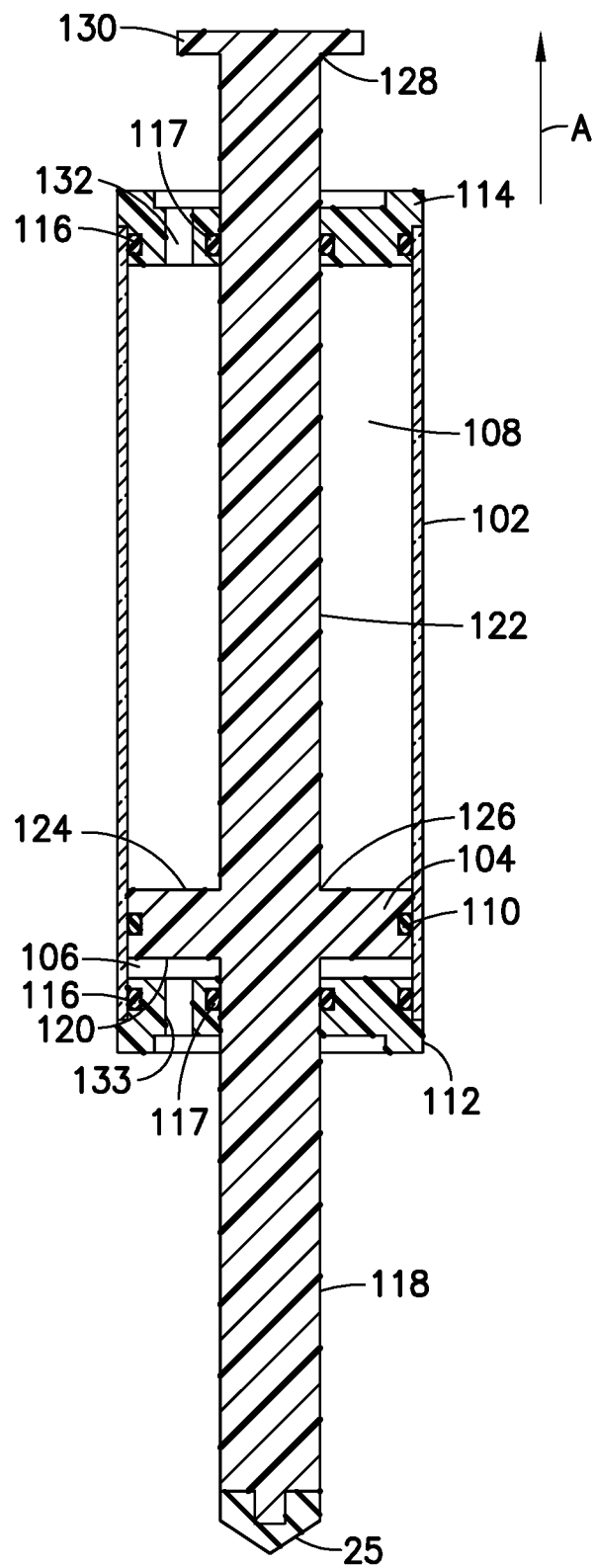
FIG. 4 is a cross-sectional view of the pressurizing mechanism of FIG. 3 taken along line 4-4.

With reference to FIGS. 3 and 4, and with continued reference to FIG. 2, one embodiment of the pressurizing mechanism 40 includes a substantially closed cylindrical body 102 having a movable member 104 positioned therein that divides the body into a first chamber 106 and a second chamber 108. The movable member 104 includes a seal 110 extending around a circumference thereof to fluidly isolate the first chamber 106 from the second chamber 108. The cylindrical body 102 is substantially closed by a first end cap 112 and a second end cap 114. The end caps 112, 114 may be formed as separate pieces or may be integrally formed with the cylindrical body 102. If the end caps 112, 114 are formed as separate pieces, they may be provided with seals 116 to prevent fluid (i.e., air) from leaving the cylindrical body 102.

A plunger rod 118 is connected to a first side 120 of the movable member 104 and extends through the first end cap 112 of the body. A seal 117 is provided between the first end cap 112 and the plunger rod 118 to prevent fluid from leaving the cylindrical body 102. The plunger rod 118 is configured to operatively engage the plunger 25 when the syringe 20 is connected to the first end cap 112 of the body 102. The pressurizing mechanism 40 also includes an elongated member 122 connected to a second side 124 of the movable member 104 and extending through the second end cap 114 of the body 102. A seal 117 is provided between the second end cap 114 and the elongated member 122 to prevent fluid from leaving the cylindrical body 102. In the embodiment of the pressurizing mechanism 40 illustrated in FIGS. 3 and 4, the elongated member 122 may be a rod having a first end 126 connected to the second side 124 of the movable member 104 and a second end 128 extending through the second end cap 114 of the body 102. The second end 128 of the rod includes a handle 130, thereby allowing a user to manually move the movable member 104 toward the second end cap 114 of the body 102 by pulling on the handle 130 in the direction of arrow A.

The pressurizing mechanism 40 further includes a valve or opening 132 positioned on the second end cap 114 in fluid communication with the second chamber 108. Desirably, the valve 132 is a removable, one-way check valve. Alternatively, the valve 132 may be a manually operable stop-cock. Still, further, the valve 132 may be removed and an opening may be provided in the second end cap 114. The purpose of the valve 132 will be discussed hereinafter. In addition, a second valve 133 may be provided in the first end cap 112. The purpose of the second valve 133, which may be embodied as a one-way check valve, is to allow the pressurizing mechanism 40 to be shipped without a vacuum provided in either the first chamber 106 or the second chamber 108. By having valves 132, 133, embodied as one-way check valves, positioned at both ends of the cylindrical body 102, a user can form the vacuums in chambers 106, 108.

Figure 5:
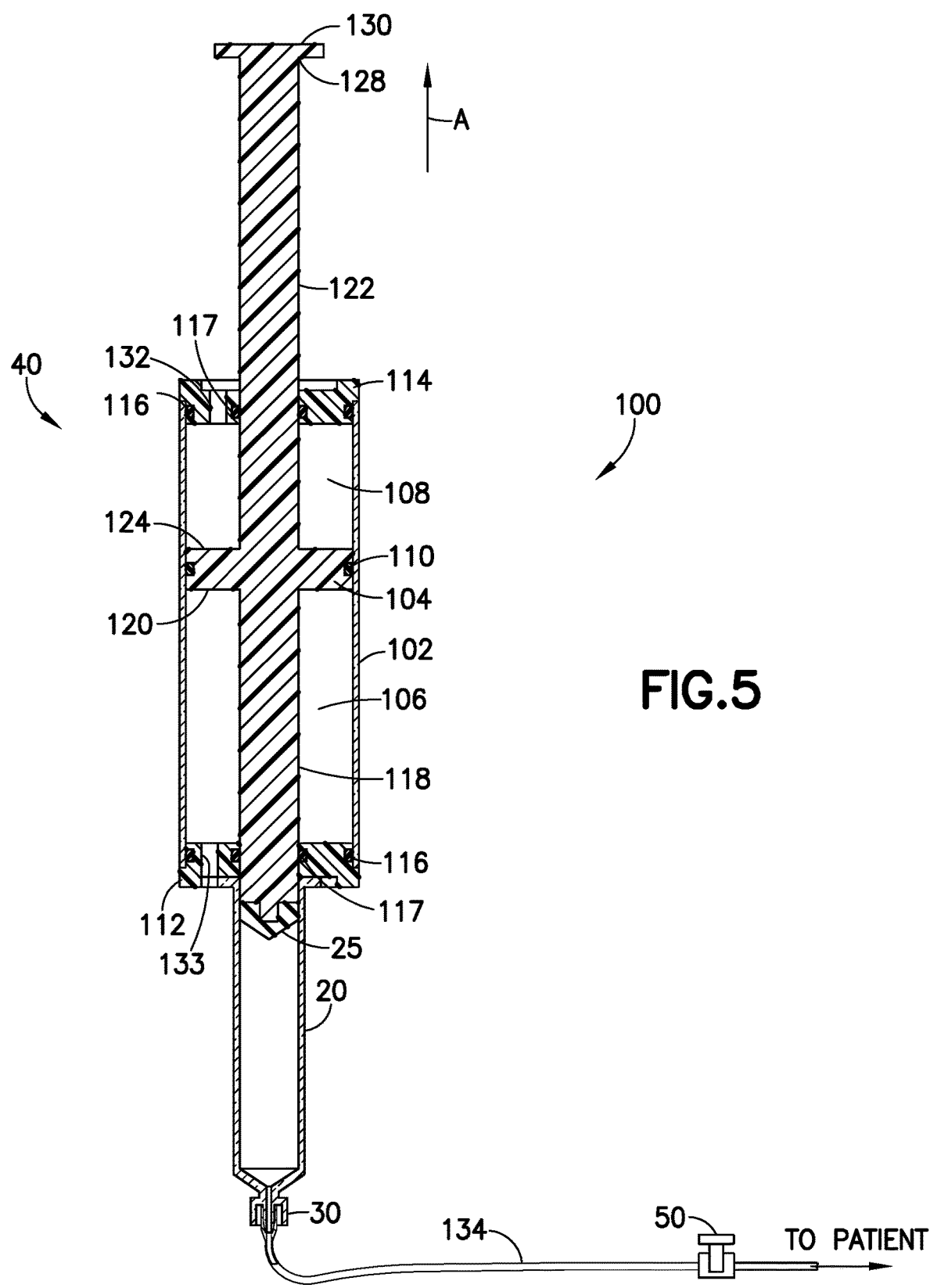
FIG. 5 is an enlarged cross-sectional view of the injection device of the system of FIG. 2 prior to actuation of the device for delivering a fluid to a patient.
Figure 6:
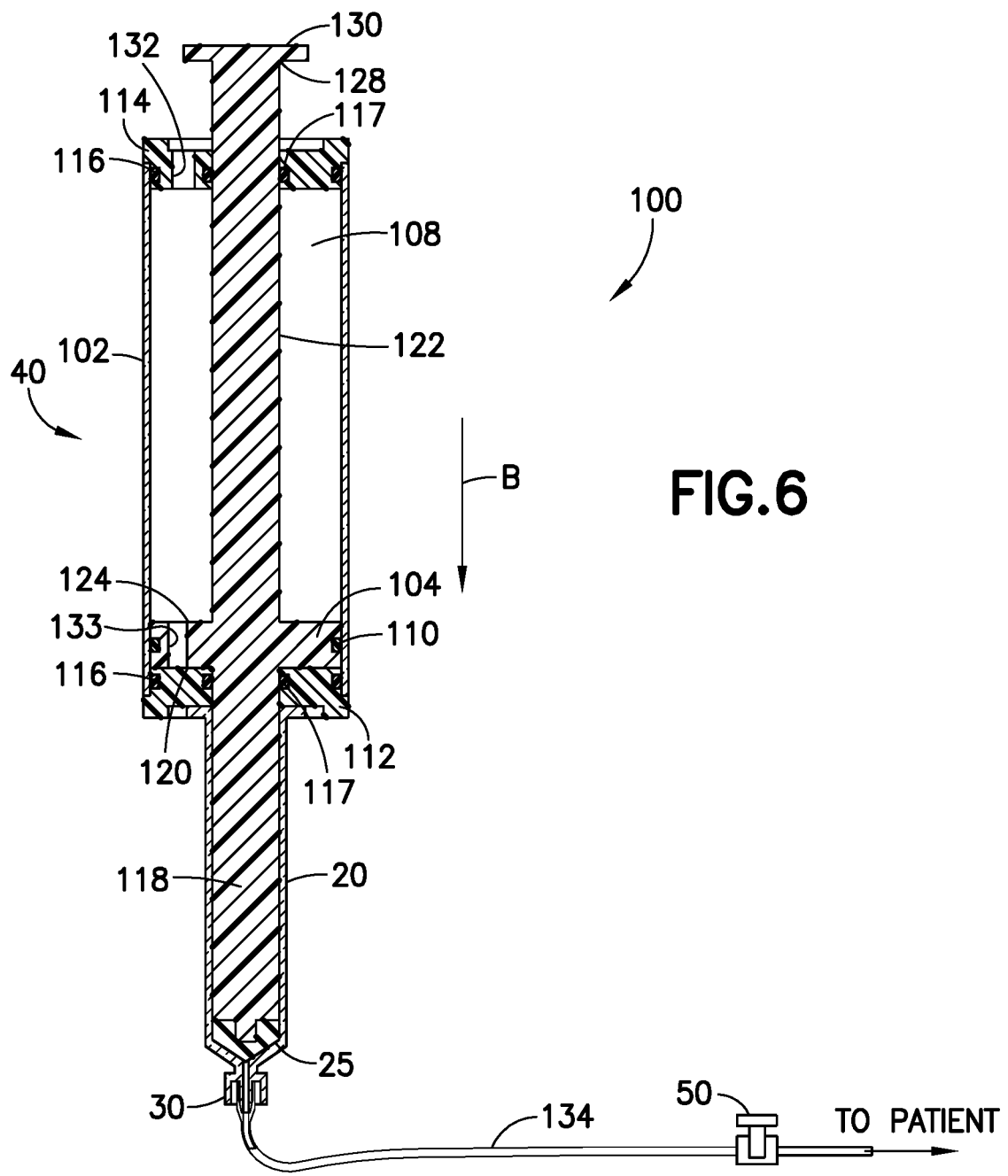
FIG. 6 is an enlarged cross-sectional view of the injection device of the system of FIG. 2 after fluid has been delivered to a patient.

With reference to FIGS. 5 and 6, and with continued reference to FIGS. 3 and 4, a disposable fluid set 134 is provided to be connected between the outlet 30 of the syringe 20 and a patient (not shown). The disposable fluid set may require less than three inches of connective tubing. Desirably, no more than one foot of connective tubing is required between the injection devices of the present invention and the injection point on the patient. Given the proximity of placement of the injection device 100 to the patient, no saline flush to remove expensive contrast medium from the fluid path is required as is often necessary with current powered injectors in which long lengths of connective tubing are required. The injection device 100 also includes an actuator 50, discussed in greater detail hereinabove, connected to the outlet 30 of the syringe 20. Desirably, the actuator 50 is positioned within the disposable fluid set 134. The actuator 50 is switchable between a first state in which fluid is prevented from flowing through the outlet 30 of the syringe 20 and a second state in which the fluid can flow through the outlet 30 of the syringe 20.

With continued reference to FIGS. 3-6, the operation of the injection device 100 will be described. First, the movable member 104 is moved toward the second end cap 114 of the body 102 when a user pulls on the handle 130 of the elongated member 122 in the direction of arrow A. As the movable member 104 is drawn rearward, a vacuum is created in the first chamber 106, air is expelled from the second chamber 108 through the one-way check valve 132, and fluid is drawn into the syringe 20. The syringe 20 can thereby be filled and the first chamber 106 can thereby be "primed" by having a vacuum developed in the first chamber 106 by an operator before a procedure. Once the air has been expelled from the second chamber 108, advancement of the movable member 104 towards the first end cap 112 creates a vacuum in the second chamber 108 that balances the vacuum in the first chamber 106. Alternatively, the device 100 can be shipped with the syringe 20 prefilled and the first and second chambers 106 and 108 "preprimed" Likewise, the injection device 100 can alternatively be shipped with the first and second chambers 106 and 108 "preprimed" and a prefilled syringe installed on location.

Once the movable member 104 has been drawn rearward and the fluid set 134 is connected, the valve 132 is opened to allow atmospheric pressure to enter the second chamber 108. While the actuator 50 is in an "off" state, fluid cannot be injected through the syringe outlet 30 and the movable member 104 cannot move forward within the first and second chambers 106 and 108 in the direction of arrow B. This state is illustrated in FIG. 5.

After the fluid path set 134 is appropriately connected to the patient and the actuator 50 is placed in an "on" state, fluid can flow through syringe outlet 30, and atmospheric pressure will force the movable member 104 to move forward. The force created (which is proportional to atmospheric pressure multiplied by the area of the movable member 104) is transferred from plunger rod 118 and, thus, to plunger 25, thereby forcing pressurized fluid through syringe outlet 30 to be injected into the patient through the fluid path set 134.

The injection device 100 can, for example, be worn by the patient via straps (not shown). Likewise, injection device 100 can be attached to scan table 92 via any appropriate attachment device.

As set forth above, pressurized fluid flows through outlet 30 upon activation of actuator 50. A controller 70 can, for example, activate actuator 50 in a remote, wireless, or untethered manner from a control room 90. An example of such a controller 70 and actuator 50 are described in U.S. Pat. No. 7,632,245, which has been incorporated herein by reference above. More specifically, the actuator 50 may include a fluid-filled (as used herein, the term fluid refers generally to either a gas or a liquid) chamber in fluid connection with a controller via a length of tubing. The controller 70 is operable to increase the pressure within the chamber upon actuation thereof. The chamber is in operative connection with a valve mechanism that is in a normally closed state. Increasing fluid pressure in the chamber (via the controller 70) acts to place the valve in an open state. The valve mechanism is within the chamber and is separated from the fluid therein by an elastomeric material that moves upon increasing the pressure of the fluid in the chamber to place the valve mechanism in an open state.

Whether the controller 70 communicates with the remote controller 71 and the actuator 50 in an untethered or tethered (for example, via cabling) manner, such communication is preferably MR compatible as described above. Communication in an MR environment suitable for communication between the controller 70 and the actuator 50 is described, for example, in U.S. Pat. Nos. 5,494,036, 6,704,592, 7,221, 159, and 7,283,860 or International Patent Application Publication No. WO 01/92907, assigned to the assignee of the present invention, the disclosure of which is incorporated herein by reference.

With reference to FIGS. 7-13, another embodiment of the injection device 200 and pressurizing mechanism 240 are shown and, wherein, like parts are designated with like reference numerals used in the description of the foregoing embodiment. The pressurizing mechanism 240 includes a substantially closed cylindrical body 102 having a movable member 104 positioned therein that divides the body into a first chamber 106 and a second chamber 108. The movable member 104 includes a seal 110 extending around a circumference thereof to fluidly isolate the first chamber 106 from the second chamber 108. The cylindrical body 102 is substantially closed by a first end cap 112 and a second end cap 114. The end caps 112, 114 may be formed as separate pieces or may be integrally formed with the cylindrical body 102. If the end caps 112, 114 are formed as separate pieces, they may be provided with seals 116 to prevent fluid (i.e., air) from leaving the cylindrical body 102. The pressurizing mechanism 40 further includes an opening 217 in fluid communication with the second chamber 108. The opening 217 allows atmospheric pressure to enter the second chamber 108.

A plunger rod 118 is connected to a first side 120 of the movable member 104 and extending through the first end cap 112 of the body. The plunger rod 118 is configured to operatively engage the plunger 25 when the syringe 20 is connected to the first end cap 112 of the body 102. The pressurizing mechanism 40 also includes an elongated member connected to a second side 124 of the movable member 104 and extending through the second end cap 114 of the body 102. In the embodiment of the pressurizing mechanism 240 illustrated in FIGS. 7 and 8, the elongated member may be a threaded rod 202 having a first end 204 connected to the second side 124 of the movable member 104 and a second end 206 extending through the second end cap 114 of the body 102. In such an embodiment, the injection device 200 may further include a releasable nut 208 positioned over the second end cap 114 of the body 102.

Figure 7:
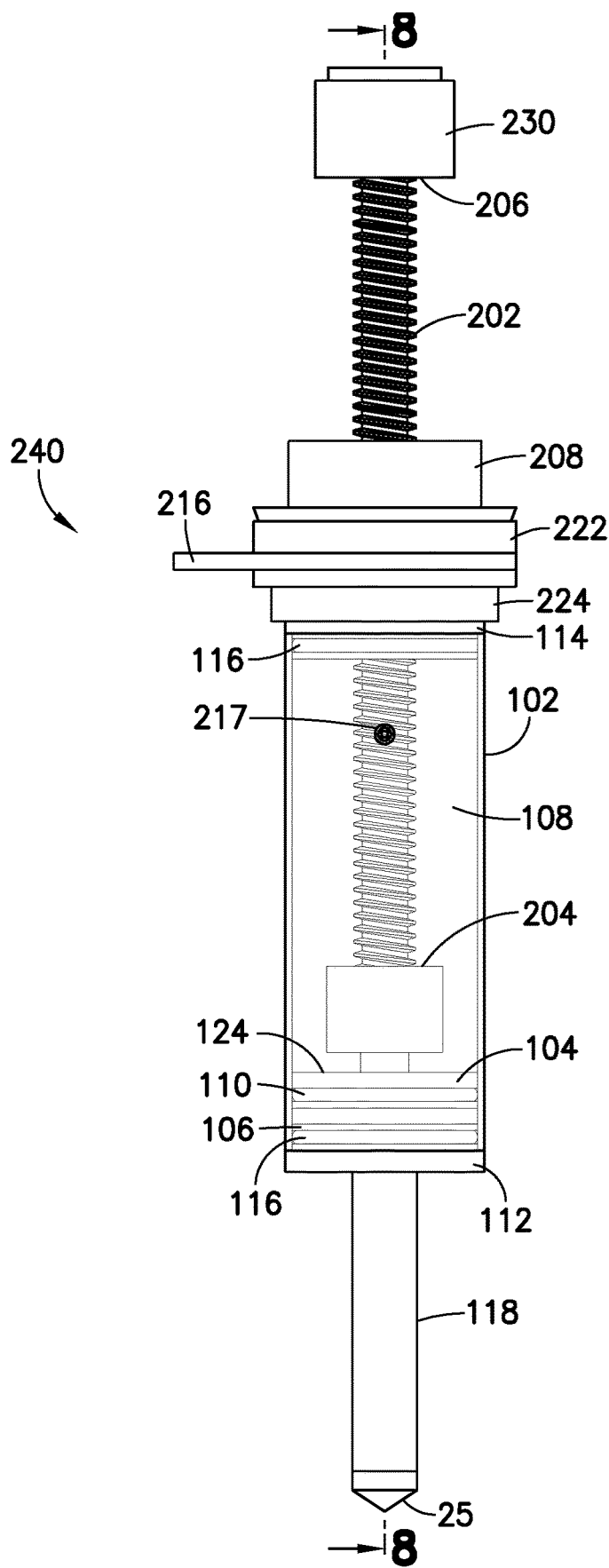
FIG. 7 is a side view of another embodiment of the pressurizing mechanism of the injection device of the system of FIG. 2.
Figure 8:
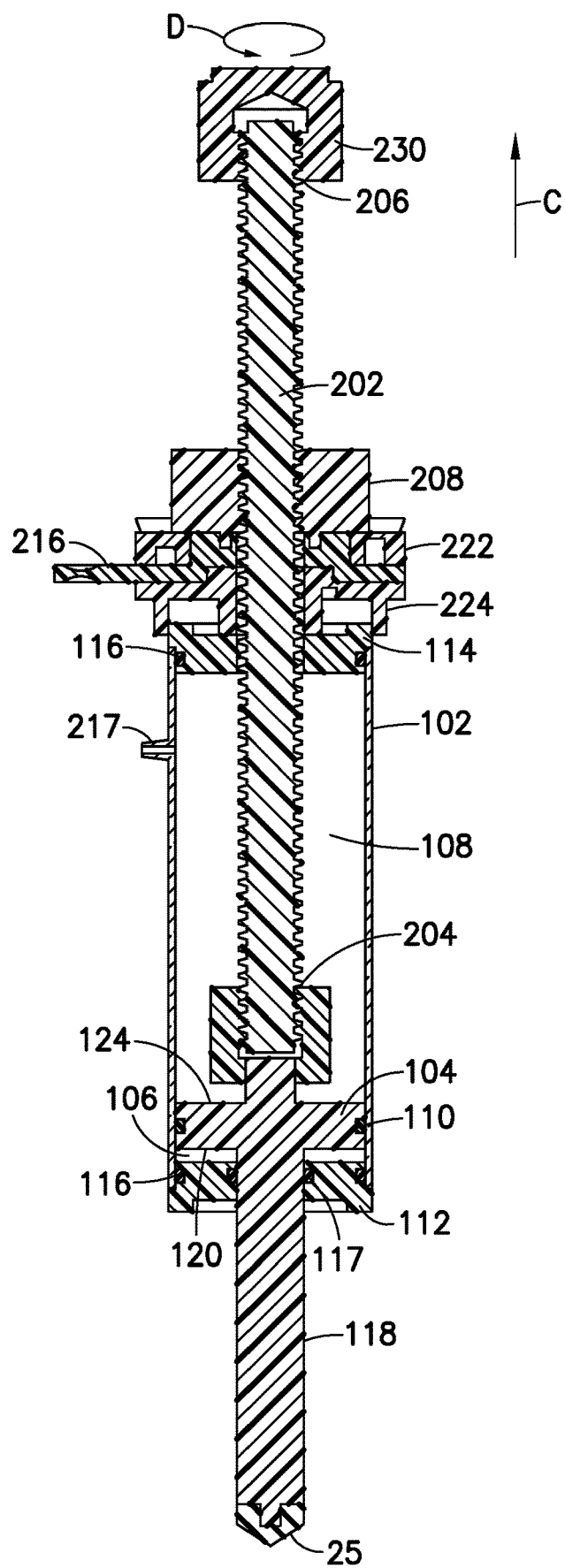
FIG. 8 is a cross-sectional view of the pressurizing mechanism of FIG. 7 taken along line 8-8.
Figure 9:
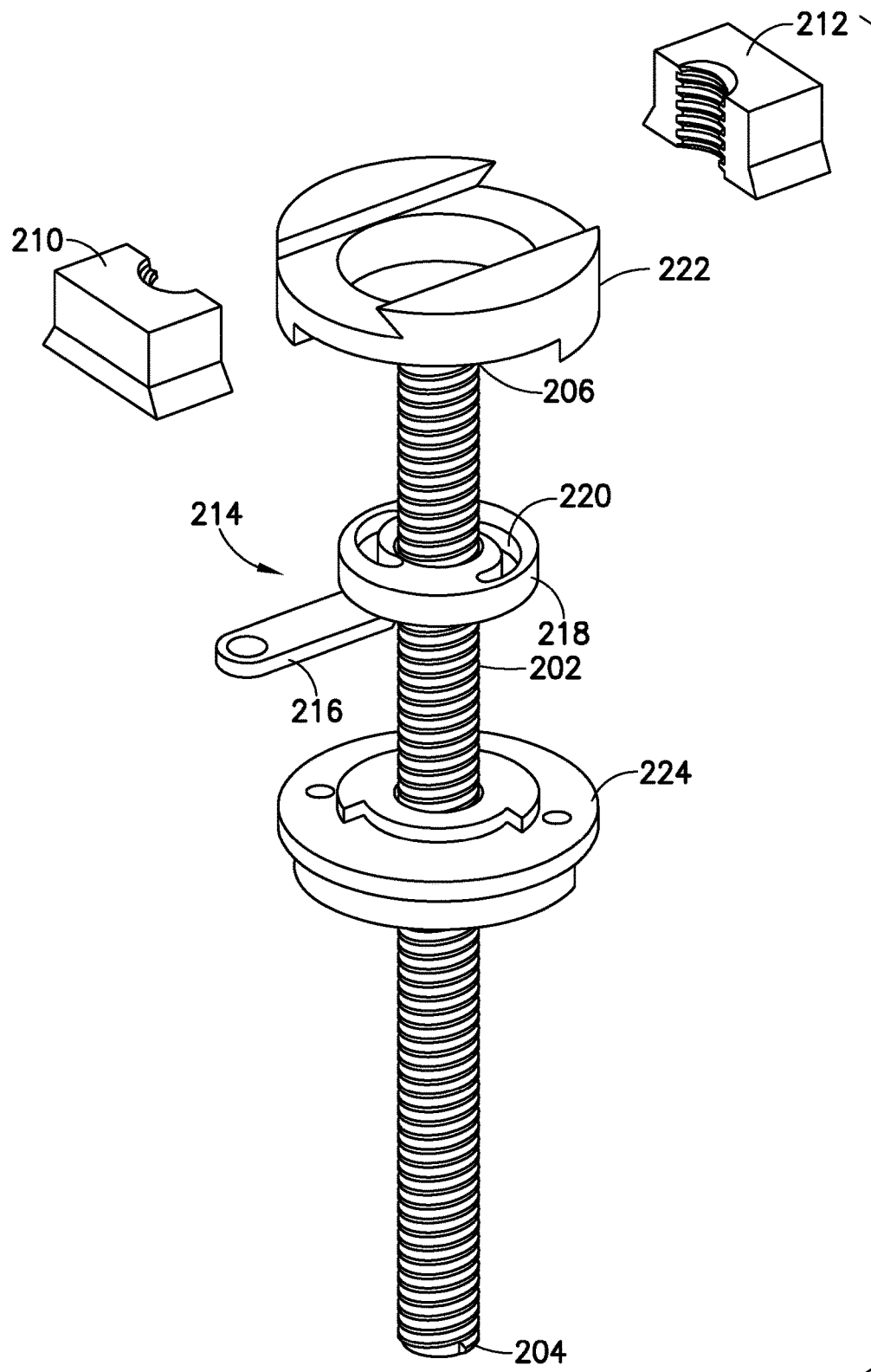
FIG. 9 is an exploded perspective view of several components of the pressurizing mechanism of FIG. 7.
Figure 10:
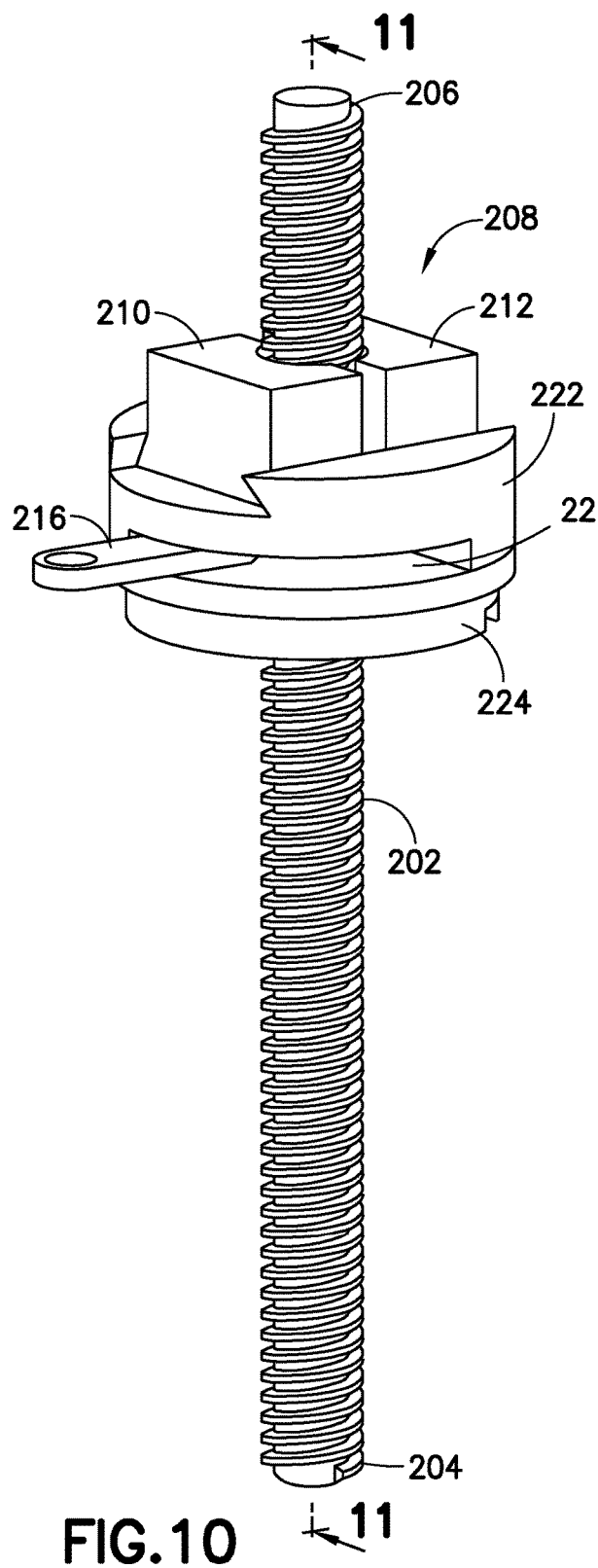
FIG. 10 is an assembled perspective view of the components of FIG. 9.
Figure 11:
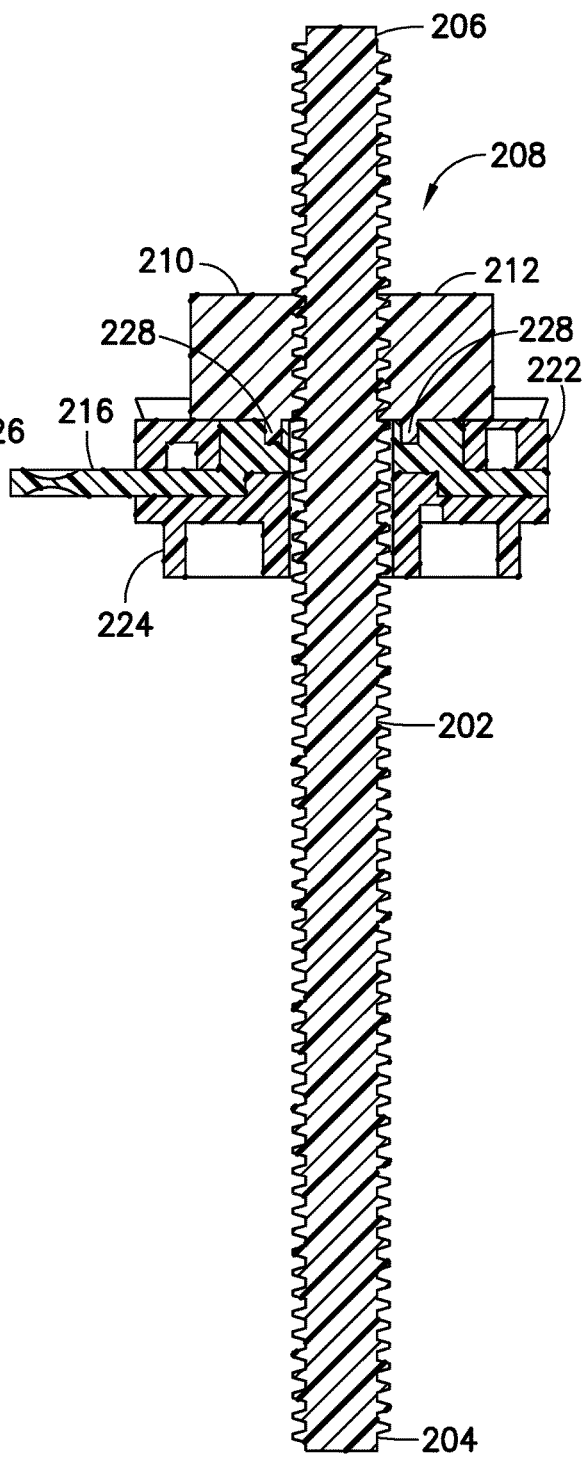
FIG. 11 is a cross-sectional view of the components of FIG. 10 taken along line 11-11.
Figure 12:
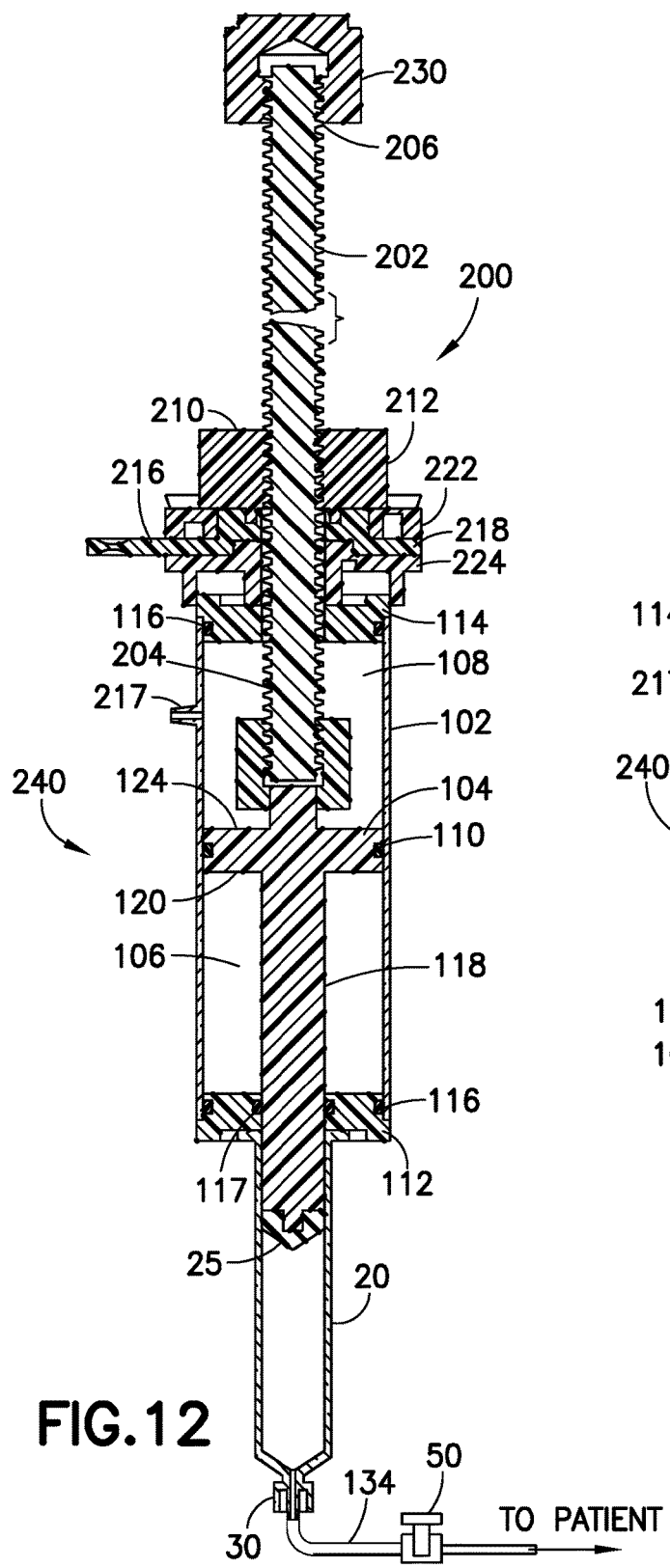
FIG. 12 is a cross-sectional view of an injection device utilizing the pressurizing mechanism of FIG. 7 prior to actuation of the device for delivering a fluid to a patient.
Figure 13:
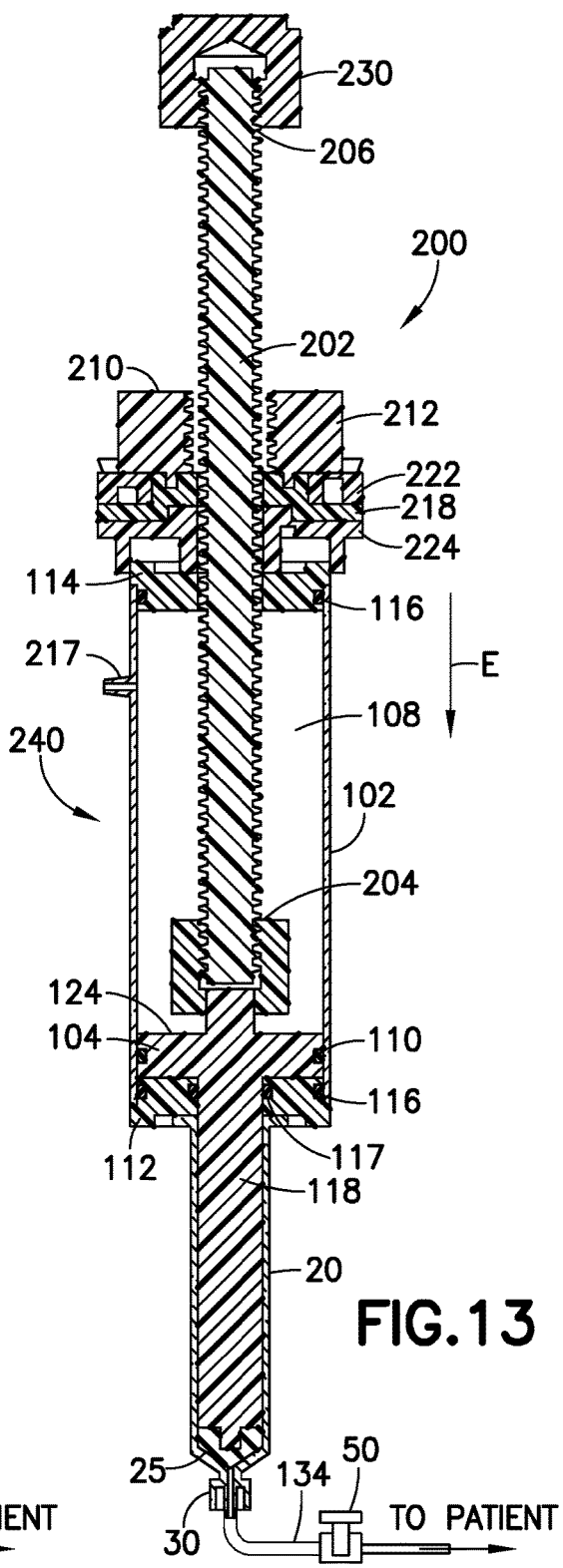
FIG. 13 is a cross-sectional view of an injection device utilizing the pressurizing mechanism of FIG. 7 after fluid has been delivered to a patient.

With reference to FIGS. 9-11, and with continued reference to FIGS. 7 and 8, the releasable nut 208 includes at least a first portion 210 and, desirably, a second portion 212 that are configured to secure the threaded rod 202 when in a closed position (see FIG. 12) and release the threaded rod 202 when in a released position (see FIG. 13). The thread of the threaded rod 202 is designed such that axial force on the threads thereof does not cause the threaded rod 202 to turn (for example, a double start Acme thread, a buttress thread, etc.). A lever mechanism 214 is provided that includes a lever 216 and a body member 218 having a track 220 formed therein. The lever mechanism 214 is enclosed at the second end cap 114 of the body 102 within an upper housing 222 and a lower housing 224. The upper and lower housings 222, 224 enclose the lever mechanism 214 such that a channel 226 is formed through which the lever 216 can travel from a first position to a second position. The releasable nut 208 further includes extension members 228 formed on the bottom portions of the first and second portions 210, 212. These extension members 228 extend into the track 220 such that when the lever 216 is in the first position, the nut 208 is closed around the threaded rod 202 and when the lever 216 is in the second position, the nut 208 is released from the threaded rod 202. The second end 206 of the threaded rod 202 includes a handle 230, thereby allowing a user to manually move the movable member 104 toward the second end cap 114 of the body 102. More specifically, the threaded rod 202 is configured to be rotated in the direction of arrow D by a user to move the moveable member 104 toward the second end cap 114 of the body 102 in the direction of arrow C with the nut 208 in the closed position.

With reference to FIGS. 12 and 13, and with continued reference to FIGS. 7-11, a disposable fluid set 134 is provided to be connected between the outlet 30 of the syringe 20 and a patient (not shown). The disposable fluid set may require less than three inches of connective tubing. Desirably, no more than one foot of connective tubing is required between the injection devices of the present invention and the injection point on the patient. As discussed hereinabove, given the proximity of placement of the injection device 200 to the patient, no saline flush to remove expensive contrast medium from the fluid path is required as is often necessary with current powered injectors in which long lengths of connective tubing are required. The injection device 200 also includes an actuator 50, discussed in greater detail hereinabove, connected to the outlet 30 of the syringe 20. Desirably, the actuator 50 is positioned within the disposable fluid set 134. The actuator 50 is switchable between a first state in which fluid is prevented from flowing through the outlet 30 of the syringe 20 and a second state in which the fluid can flow through the outlet 30 of the syringe 20.

With continued reference to FIGS. 7-13, the operation of the injection device 200 will be described. First, the movable member 104 is moved toward the second end cap 114 of the body 102 in the direction of arrow C when a user rotates the handle 230 in the direction of arrow D with the nut 208 in the closed position around the threaded rod 202. As the movable member 104 is drawn rearward, a vacuum is created in the first chamber 106 and fluid is drawn into the syringe 20. The opening 217 maintains the second chamber at atmospheric pressure. The syringe 20 can thereby be filled and the first chamber 106 can thereby be "primed" by an operator before a procedure. Alternatively, the injection device 100 can be shipped with the syringe 20 prefilled and the first chamber 106 "preprimed". Likewise, the injection device 100 can alternatively be shipped with the first chamber 106 "preprimed" and a prefilled syringe installed on location.

Once the movable member 104 has been drawn rearward, the fluid path set 134 is coupled to the fluid delivery device 200 with the actuator 50 in the off state. The lever 216 is then rotated to the second position to move the first portion 210 and the second portion 212 of the nut 208 out of contact with the threaded rod 202. While the actuator 50 is in an "off" state, fluid cannot be injected through the syringe outlet 30 and the movable member 104 cannot move forward within the first and second chambers 106 and 108 in the direction of arrow E. After the fluid path set 134 is appropriately connected to the patient and the actuator 50 is placed in an "on" state, fluid can flow through syringe outlet 30 and atmospheric pressure will force the movable member 104 to move forward. The force created (which is proportional to atmospheric pressure multiplied by the area of the movable member 104) is transferred from plunger rod 118 and, thus, to plunger 25, thereby forcing pressurized fluid through syringe outlet 30 to be injected into the patient through the fluid path set 134.

The injection device 200 can also be worn by the patient via straps (not shown) or attached to scan table 92 via any appropriate attachment device.

As set forth above, pressurized fluid flows through outlet 30 upon activation of actuator 50. A controller 70 can, for example, activate actuator 50 in a remote, wireless, or untethered manner from a control room 90 as discussed hereinabove. In addition, a sensor may be provided to determine the position of the threaded rod 202 and provide this information to the controller 70. More specifically, when delivering contrast (in MR, CT, or Angiographic procedures) or exposing a patient to radiation (CT) it is important to record many events such as: the time of the procedure; the rate the contrast was delivered; the amount of contrast; and the amount of radiation exposure. A syringe that could record some of this information would be very valuable to the clinician. Accordingly, fluid delivery device 200 may include sensors that would be tied into an "informatics" system. The informatics system could then analyze, record, and adjust analytic functions based on the readings from the sensors.

With reference to FIGS. 20-23, the sensor(s) may be embodied in a variety of different manners. For instance, with specific reference to FIG. 20, the sensor may be embodied as an optical reflective sensor assembly 502 positioned adjacent to the threaded rod 202 of the fluid delivery system 200. The optical reflective sensor assembly 502 includes an emitter portion 504 for emitting an optical signal 506 and a receiver portion 508 for receiving the optical signal 506 after it has been reflected from the surface of the threaded rod 202. In operation, as the threaded rod 202 moves by the fixed position of the optical reflective sensor assembly 502, the output signal of the receiver portion 508 will imitate the low and high areas of the rod as shown in FIG. 20. The output signal of the receiver portion 508 can then be processed to convey various parameters of the performance and operation of the fluid delivery system 200. For example, if the number of high to low transitions is counted, the distance traveled by the threaded rod 202 can be determined and thus the volume delivered could be derived. In addition, if the number of transitions is referenced to a time base then the flow rate of the fluid delivery system 200 can be expressed. Furthermore, absolute positional information of the threaded rod 202 can be obtained by detecting unique features 510 of the threaded rod 202, such as the beginning or the end of travel of the threaded rod 202.

Much of the same information can also be obtained from alternate types of sensor assemblies. For example, with reference to FIG. 21, an encoder sensor assembly 512 may be provided with an attached wheel and/or gear 514 in contact with the threaded rod 202 to obtain a similar output as the optical reflective sensor assembly 502 discussed hereinabove.

In addition, with reference to FIG. 22, a potentiometer assembly 516 connected to a wheel 518 in contact with the threaded rod 202 may be provided as the sensor. In this case, an analog output would result representing the distance traveled with the added feature of conveying the absolute position of the threaded rod 202.

With reference to FIG. 23, the sensor may further be embodied as an optical slotted detector assembly 520. This assembly is similar to the optical reflective sensor assembly 502, except the optical beam is passed through or blocked by the rotation of the wheel 522 in contact with the threaded rod 202.

Yet another example of a sensor that could be utilized is that the threaded rod 202 could be hollow with a tapered inside. An ultrasonic sensor could be used to "measure" the thickness of the material. This would provide an absolute position and could measure the rate at which the "thickness" changed. This would provide a rate of the piston movement which could equate to flow rate and volume delivered.

Figure 14:
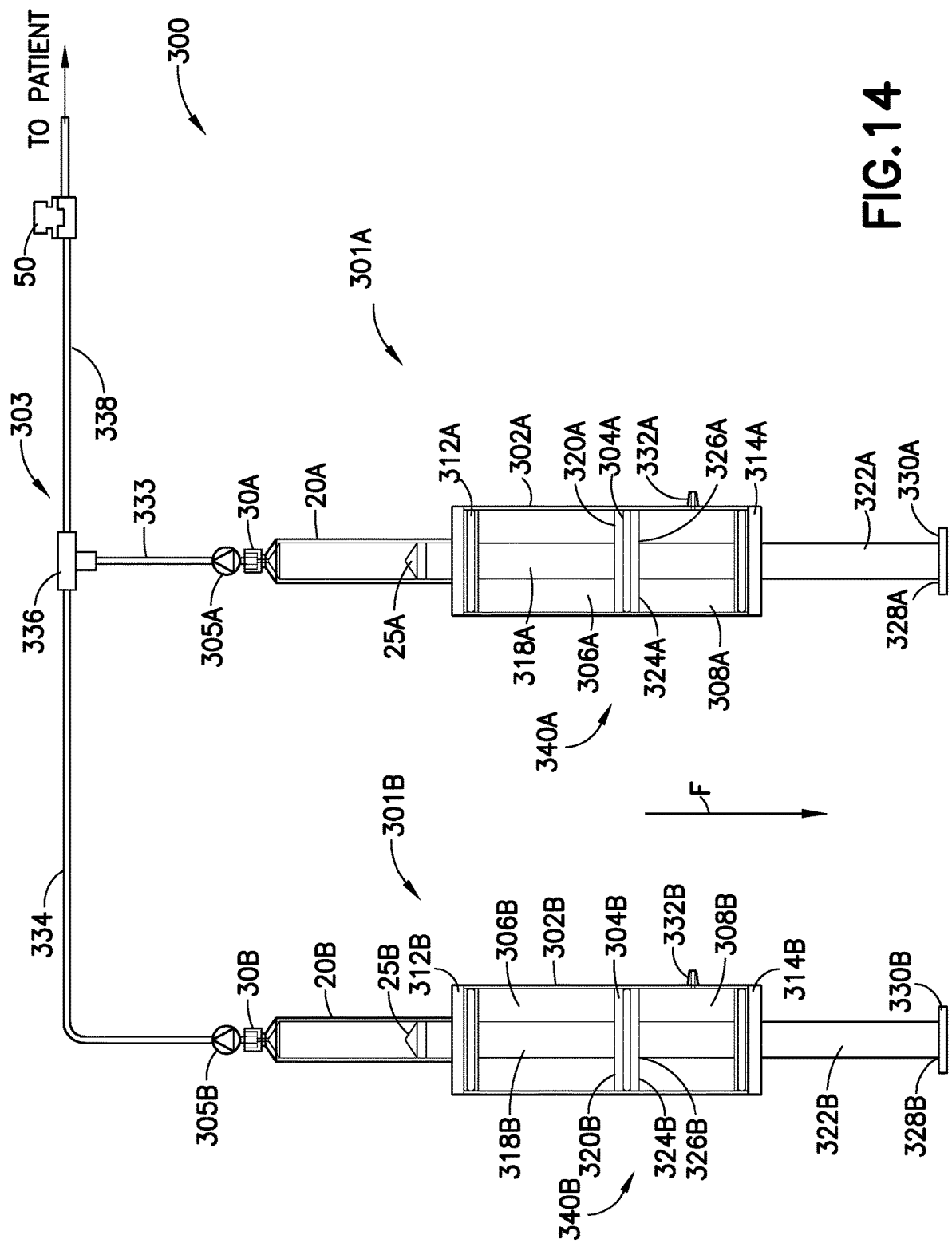
FIGS. 14-16 are side views of a fluid delivery system in accordance with the present invention for delivering a first fluid followed by a second fluid prior to injecting either fluid, after the first fluid has been injected, and after both fluids have been delivered, respectively.
Figure 15:
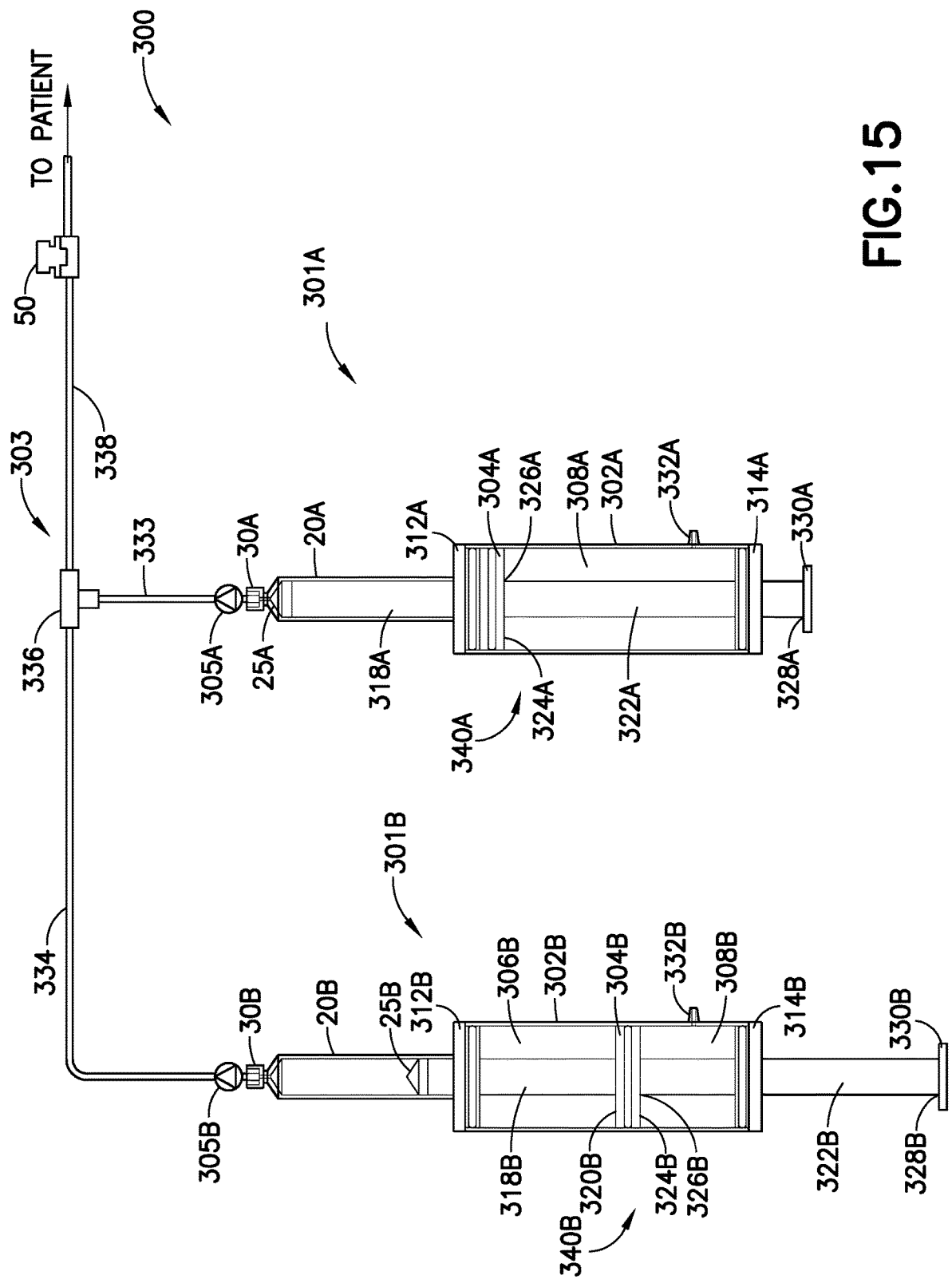
Figure 16:
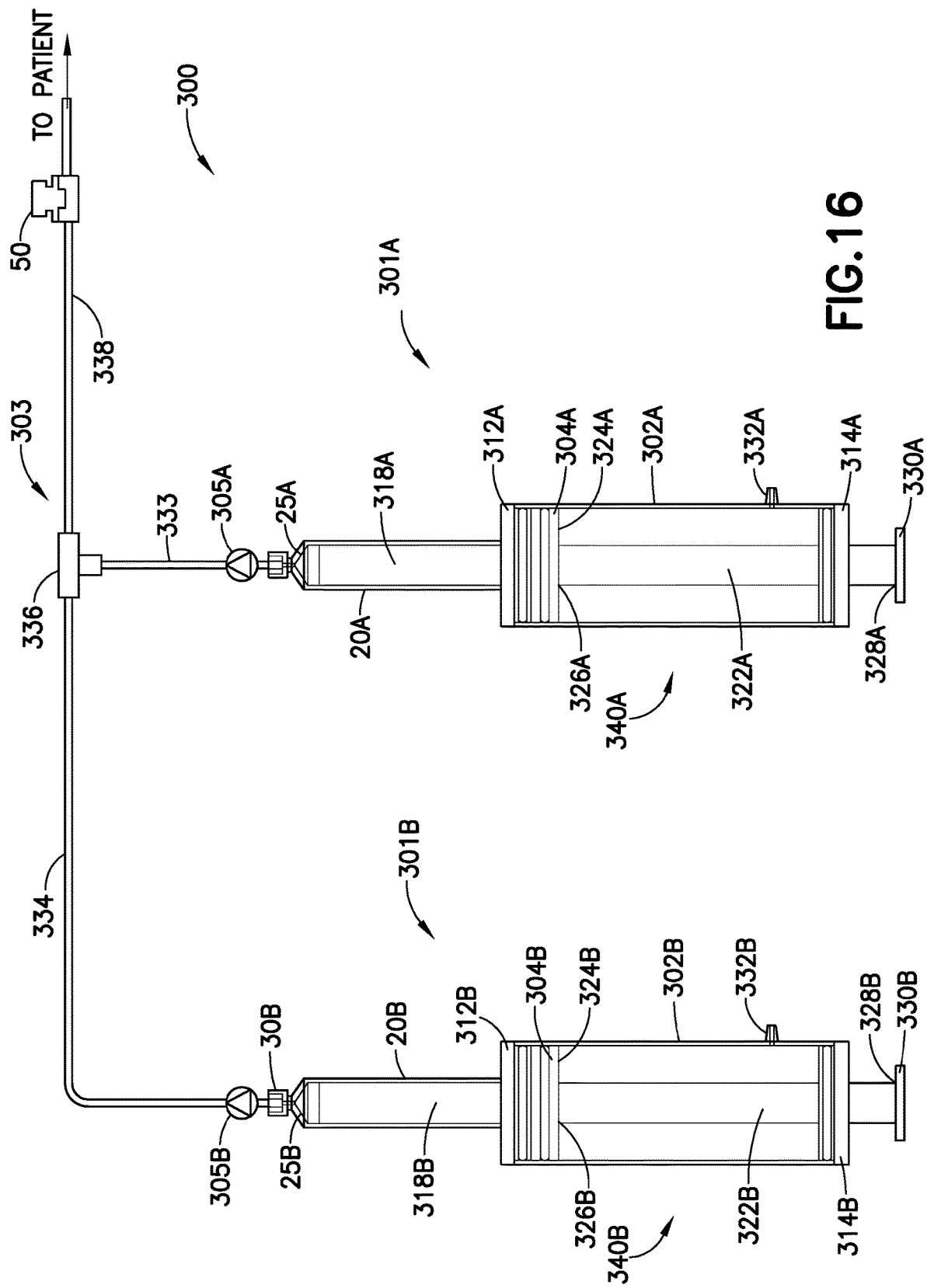

With reference to FIGS. 14-16, while it has been described hereinabove that a saline flush is not required, in certain instances, it may be desirable to follow the injection of an injection fluid (for example, contrast medium, stress agents, saline, blood pool agents and/or organ specific agents) with an injection of saline, contrast, or other fluids. For instance, some procedures like dynamic MR studies or cardiac MR require a saline flush at the end of the procedure. Accordingly, a fluid delivery system 300 is provided that includes MR compatible parts. More specifically, the fluid delivery system 300 includes a first injection device 301A, a second injection device 301B, a fluid path set 303, an actuator 50, a first one-way check valve 305A, and a second one-way check valve 305B.

The first injection device 301A and the second injection device 301B may be any of the injection devices described hereinabove or any of the injection devices described in U.S. Pat. No. 7,632,245. For explanatory purposes, the fluid delivery system 300 will be described as including injection devices similar to those illustrated in FIGS. 5 and 6. More specifically, the first injection device 301A includes a first syringe 20A having a substantially cylindrical syringe barrel having an outlet 30A and an open end. The first syringe 20A further includes a plunger 25A configured to be received within the open end of the syringe barrel. A fluid is provided within the syringe barrel. The fluid may be contrast or a stress agent.

The first injection device 301A further includes a first pressurizing mechanism 340A. The first pressurizing mechanism 340A includes: a substantially cylindrical body 302A having a movable member 304A positioned therein that divides the body 302A into a first chamber 306A and a second chamber 308A. The first pressurizing mechanism 340A further includes a plunger rod 318A connected to a first side 320A of the movable member 304A and extending through a first end cap 312A of the body 302A. The plunger rod 318A is configured to operatively engage the plunger 25A when the first syringe 20A is connected to the first end cap 312A of the body 302A.

The first pressurizing mechanism 340A also includes an elongated member 322A connected to a second side 324A of the movable member 304A and extending through a second end cap 314A of the body 302A. The elongated member 322A may be a rod having a first end 326A connected to the second side 324A of the movable member 304A and a second end 328A extending through the second end cap 314A of the body 302A. The second end 328A of the rod includes a handle 330A, thereby allowing a user to manually move the movable member 304A toward the second end cap 314A of the body 302A by pulling the handle 330A away from the second end cap 314A. The pressurizing mechanism 340A further includes a valve 332A positioned on the body 302A adjacent to the second chamber 308A.

The second injection device 301B includes a second syringe 20B having a substantially cylindrical syringe barrel having an outlet 30B and an open end. The second syringe 20B further includes a plunger 25B configured to be received within the open end of the syringe barrel. A fluid is provided within the syringe barrel. The fluid may be saline.

The second injection device 301B further includes a second pressurizing mechanism 340B. The second pressurizing mechanism 340B includes: a substantially cylindrical body 302B having a movable member 304B positioned therein that divides the body 302B into a first chamber 306B and a second chamber 308B. The second pressurizing mechanism 340B further includes a plunger rod 318B connected to a first side 320B of the movable member 304B and extending through a first end cap 312B of the body 302B. The plunger rod 318B is configured to operatively engage the plunger 25B when the second syringe 20B is connected to the first end cap 312B of the body 302B.

The second pressurizing mechanism 340B also includes an elongated member 322B connected to a second side 324B of the movable member 304B and extending through a second end cap 314B of the body 302B. The elongated member 322B may be a rod having a first end 326B connected to the second side 324B of the movable member 304B and a second end 328B extending through the second end cap 314B of the body 302B. The second end 328B of the rod includes a handle 330B, thereby allowing a user to manually move the movable member 304B toward the second end cap 314B of the body 302B by pulling the handle 330B away from the second end cap 314B. The pressurizing mechanism 340B further includes a valve 332B positioned on the body 302B adjacent to the second chamber 308B.

The fluid path set 303 includes a first tubing section 333 connected to the outlet 30A of the first syringe 20A of the first injection device 301A and a second tubing section 334 connected to the outlet 30B of the second syringe 20B of the second injection device 301B. The first tubing section 333 and the second tubing section 334 are coupled together by a T-type or Y-type connector 336 and a third tubing section 338 extends from the connector 336 to the patient. The actuator 50 may be positioned within the fluid path set 303 downstream from the connector 336.

The first one-way check valve 305A is positioned at the outlet 30A of the first syringe 20A and the second one-way check valve 305B is positioned at the outlet 30B of the second syringe 20B. The second one-way check valve 305B has a crack pressure, for instance 10 psi, that is greater than a crack pressure of the first one-way check valve 305A. Alternatively, the fluid delivery system 300 may have the first one-way check valve 305A removed and would operate similarly with only the second one-way check valve 305B.

With continued reference to FIGS. 14-16, the operation of the fluid delivery system 300 will be described. First, the movable members 304A, 304B of the first and second injection devices 301A, 301B are moved toward the second end caps 314A, 314B of the bodies 302A, 302B when a user pulls on the handle 330A, 330B of the elongated members 322A, 322B in the direction of arrow F as shown in FIG. 14. As the movable members 304A, 304B are drawn rearward, a vacuum is created in the first chambers 306A, 306B, air is expelled from the second chambers 308A, 308B, and fluid is drawn into the syringes 20A, 20B. The syringes 20A, 20B can thereby be filled and the first chamber 306A, 306B can thereby be "primed" by an operator before a procedure. Once the air has been expelled from the second chambers 308A, 308B, advancement of the movable members 304A, 304B towards the first end caps 312A, 312B creates a vacuum in the second chambers 308A, 308B that balances the vacuum in the first chambers 306A, 306B. Alternatively, the devices 301A, 301B can be shipped with the syringes 20A, 20B prefilled and the first and second chambers 306A, 306B and 308A, 308B "preprimed". Likewise, the devices 301A, 301B can alternatively be shipped with the first and second chambers 306A, 306B and 308A, 308B "preprimed" and a prefilled syringe installed on location.

Once the movable members 304A, 304B have been drawn rearward, the valves 332A, 332B are opened to allow atmospheric pressure to enter the second chambers 308A, 308B. While the actuator 50 is in an "off" state, fluid cannot be injected through the syringe outlets 30A, 30B and the movable members 304A, 304B cannot move forward within the first and second chambers 306A, 306B and 308A, 308B. This state is illustrated in FIG. 14.

After the fluid path set 303 is appropriately connected to the patient and the actuator 50 is placed in an "on" state, atmospheric pressure forces the movable member 304A of the first injection device 301A to move forward. The force created is transferred from plunger rod 318A and, thus, to plunger 25A, thereby forcing pressurized fluid through syringe outlet 30A to be injected into the patient through the fluid path set 303. This state of the system is illustrated in FIG. 15. Since, the second one-way check valve 305B has a crack pressure that is greater than a crack pressure of the first one-way check valve 305A, fluid within the second syringe 20B is not delivered until the fluid within the first syringe 20A has been completely delivered. In this manner, contrast or stress agent from the first syringe can be delivered to a patient followed by a saline flush. The state in which the fluid within the second syringe 20B has been delivered is illustrated in FIG. 16.

Figure 17:
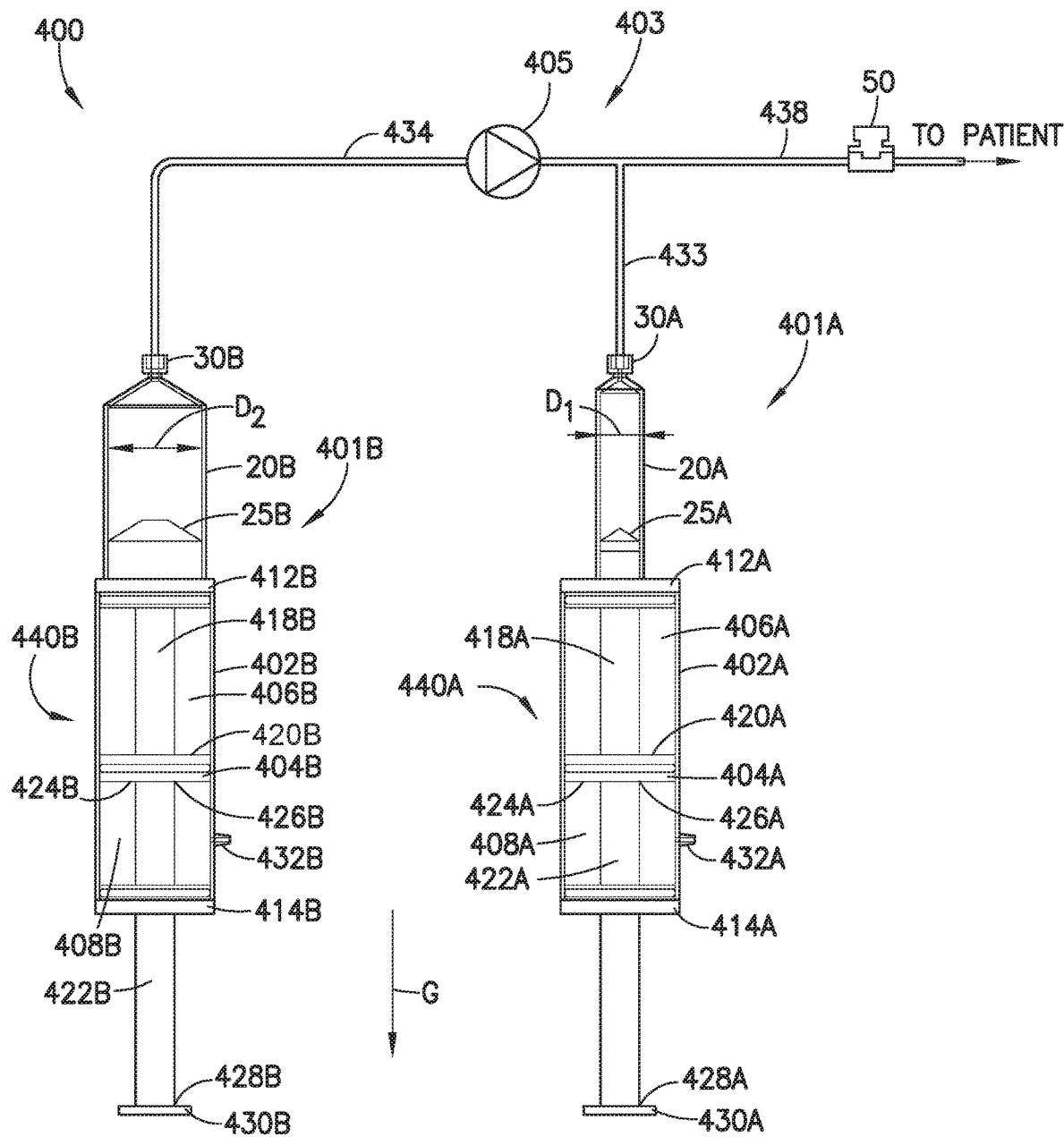
FIGS. 17-19 are side views of another embodiment of a fluid delivery system in accordance with the present invention for delivering a first fluid followed by a second fluid prior to injecting either fluid, after the first fluid has been injected, and after both fluids have been delivered, respectively.
Figure 18:
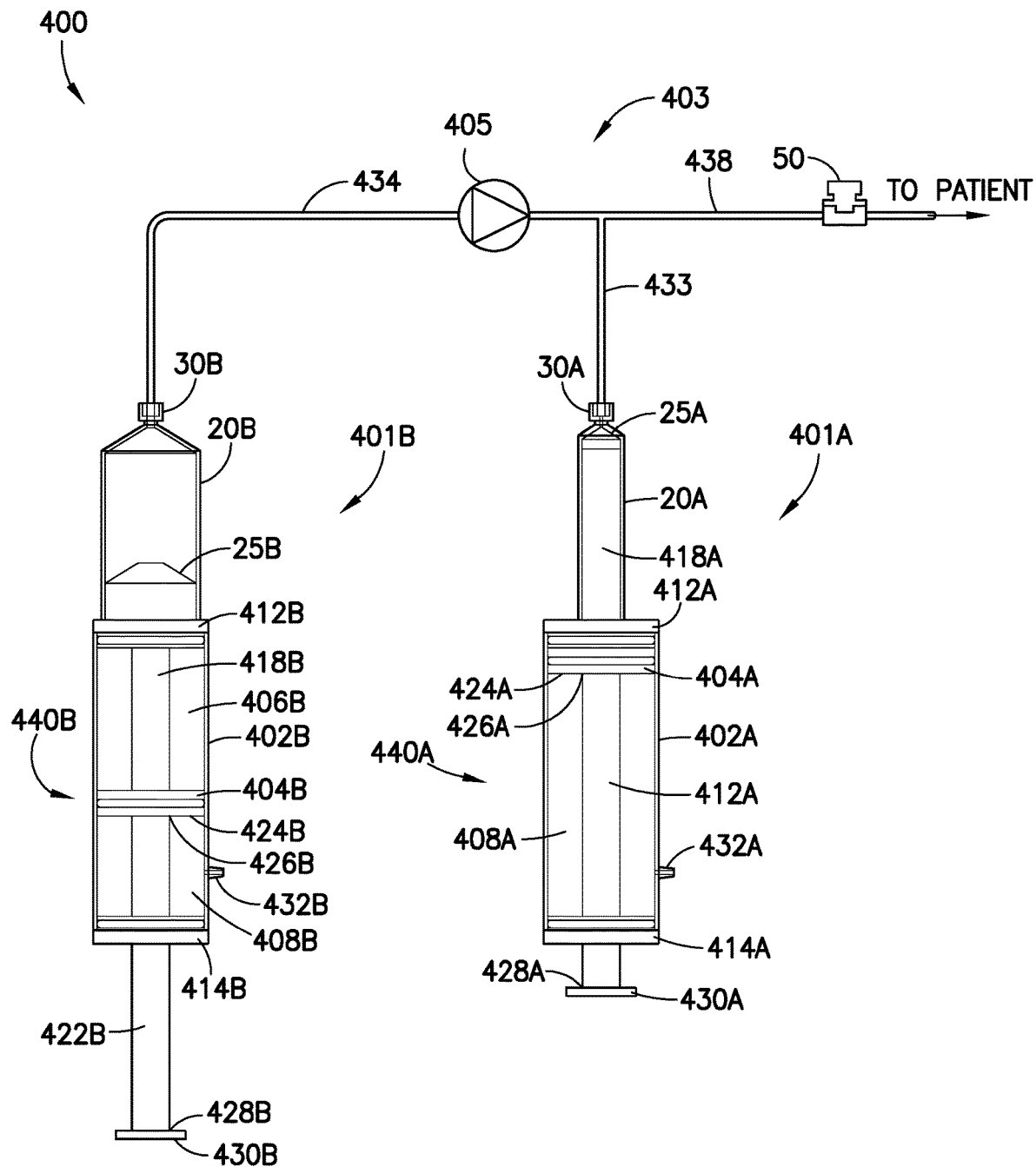
Figure 19:
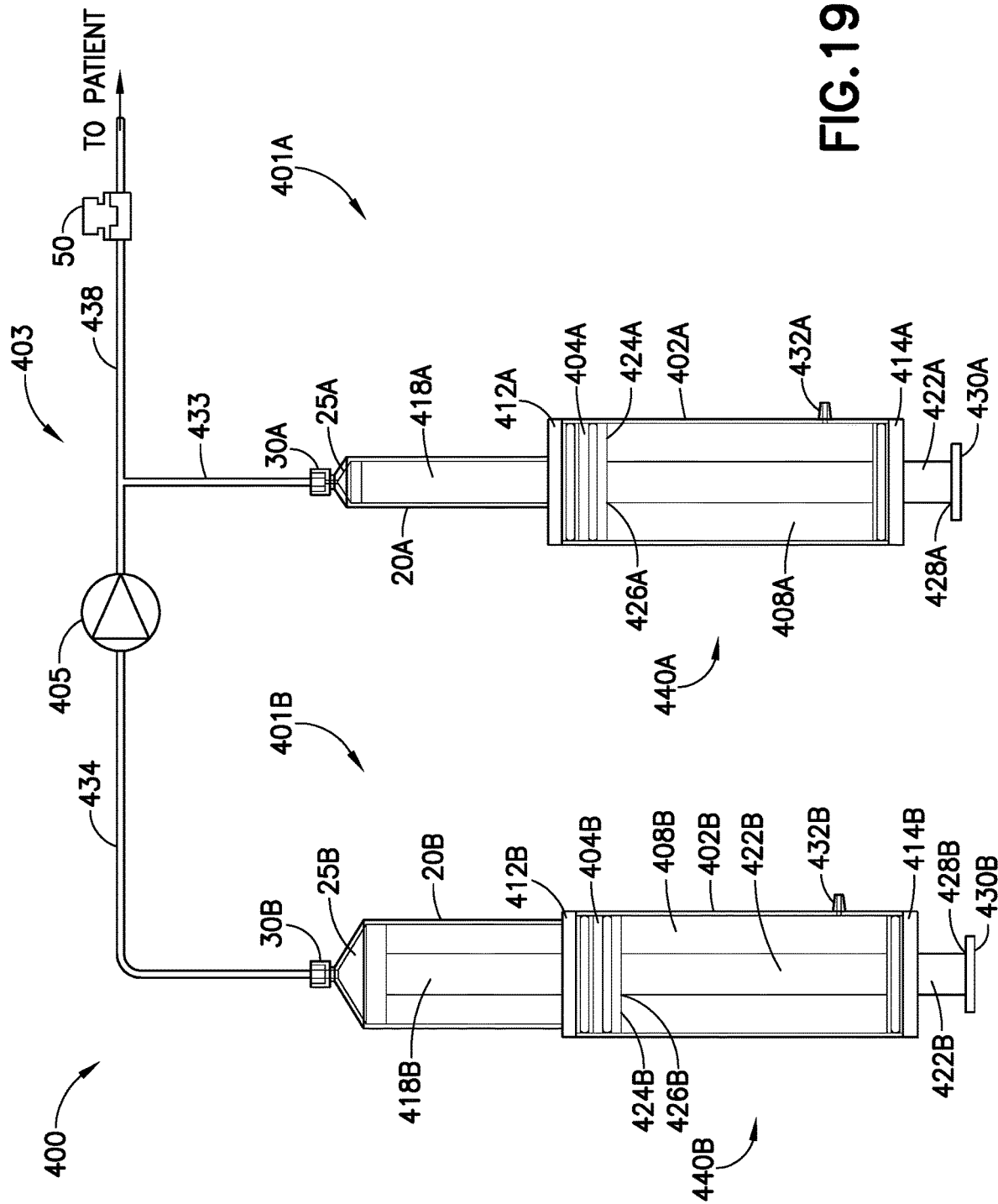

With reference to FIGS. 17-19, an alternative embodiment of a fluid delivery system 400 for delivery a first fluid followed by a saline flush is illustrated. The fluid delivery system 400 includes a first injection device 401A, a second injection device 401B, a fluid path set 403, an actuator 50, and a one-way check valve 405 positioned within the fluid path set 403.

The first injection device 401A and the second injection device 401B may be any of the injection devices described hereinabove or any of the injection devices described in U.S. Pat. No. 7,632,245. For explanatory purposes, the fluid delivery system 400 will be described as including injection devices similar to those illustrated in FIGS. 5 and 6. More specifically, the first injection device 401A includes a first syringe 20A having a substantially cylindrical syringe barrel having an outlet 30A and an open end. The first syringe 20A further includes a plunger 25A configured to be received within the open end of the syringe barrel. A fluid is provided within the syringe barrel. The fluid may be contrast or a stress agent.

The first injection device 401A further includes a first pressurizing mechanism 440A. The first pressurizing mechanism 440A includes: a substantially cylindrical body 402A having a movable member 404A positioned therein that divides the body 402A into a first chamber 406A and a second chamber 408A. The first pressurizing mechanism 440A further includes a plunger rod 418A connected to a first side 420A of the movable member 404A and extending through a first end cap 412A of the body 402A. The plunger rod 418A is configured to operatively engage the plunger 25A when the first syringe 20A is connected to the first end cap 412A of the body 402A.

The first pressurizing mechanism 440A also includes an elongated member 422A connected to a second side 424A of the movable member 404A and extending through a second end cap 414A of the body 402A. The elongated member 422A may be a rod having a first end 426A connected to the second side 424A of the movable member 404A and a second end 428A extending through the second end cap 414A of the body 402A. The second end 428A of the rod includes a handle 430A, thereby allowing a user to manually move the movable member 404A toward the second end cap 414A of the body 402A by pulling the handle 430A away from the second end cap 414A. The pressurizing mechanism 440A further includes a valve 432A positioned on the body 402A adjacent to the second chamber 408A.

The second injection device 401B includes a second syringe 20B having a substantially cylindrical syringe barrel having an outlet 30B and an open end. The second syringe 20B further includes a plunger 25B configured to be received within the open end of the syringe barrel. A fluid is provided within the syringe barrel. The fluid may be saline, contrast, or other fluids. The substantially cylindrical syringe barrel of the second syringe 20B has a diameter $D_2$ that is greater than a diameter $D_1$ of the substantially cylindrical syringe barrel of the first syringe 20A. Accordingly, the fluid within the first syringe 20A will be delivered at a higher pressure than the fluid within the second syringe 20B, thereby causing the fluid within the first syringe 20A to be delivered before the fluid within the second syringe 20B as discussed in greater detail hereinafter. The same effect can be achieved by providing the first pressurizing mechanism 440A with a cylindrical body 402A that has a greater diameter than the diameter of the cylindrical body 402B of the second pressurizing mechanism 440B given that the diameters of the first syringe 20A and the second syringe 20B are the same.

The second injection device 401B further includes a second pressurizing mechanism 440B. The second pressurizing mechanism 440B includes: a substantially cylindrical body 402B having a movable member 404B positioned therein that divides the body 402B into a first chamber 406B and a second chamber 408B. The second pressurizing mechanism 440B further includes a plunger rod 418B connected to a first side 420B of the movable member 404B and extending through a first end cap 412B of the body 402B. The plunger rod 418B is configured to operatively engage the plunger 25B when the second syringe 20B is connected to the first end cap 412B of the body 402B.

The second pressurizing mechanism 440B also includes an elongated member 422B connected to a second side 424B of the movable member 404B and extending through a second end cap 414B of the body 402B. The elongated member 422B may be a rod having a first end 426B connected to the second side 424B of the movable member 404B and a second end 428B extending through the second end cap 414B of the body 402B. The second end 428B of the rod includes a handle 430B, thereby allowing a user to manually move the movable member 404B toward the second end cap 414B of the body 402B by pulling the handle 430B away from the second end cap 414B. The pressurizing mechanism 440B further includes a valve 432B positioned on the body 402B adjacent to the second chamber 408B.

The fluid path set 403 includes a first tubing section 433 connected to the outlet 30A of the first syringe 20A of the first injection device 401A and to the one-way check valve 405. The fluid path set 403 also includes a second tubing section 434 connected to the outlet 30B of the second syringe 20B of the second injection device 401B and a third tubing section 438 extending from the one-way check valve 405 to the patient. The second tubing section 434 intersects the third tubing section 438 between the one-way check valve 405 and the patient. The actuator 50 may be positioned within the fluid path set 403 downstream from the one-way check valve 405.

The one-way check valve 405 is positioned at the outlet 30B of the second syringe 20B as described hereinabove. The one-way check valve 405 prevents the fluid in the first syringe 20A from entering into the second syringe 20B through the second tubing section 434 because the fluid in the first syringe 20A has a higher pressure since the first syringe 20A has a smaller diameter than the second syringe 20B.

With continued reference to FIGS. 17-19, the operation of the fluid delivery system 400 will be described. First, the movable members 404A, 404B of the first and second injection devices 401A, 401B are moved toward the second end caps 414A, 414B of the bodies 402A, 402B when a user pulls on the handle 430A, 430B of the elongated members 422A, 422B in the direction of arrow G as shown in FIG. 17. As the movable members 404A, 404B are drawn rearward, a vacuum is created in the first chambers 406A, 406B, air is expelled from the second chambers 408A, 408B, and fluid is drawn into the syringes 20A, 20B. The syringes 20A, 20B can thereby be filled and the first chamber 406A, 406B can thereby be "primed" by an operator before a procedure. Once the air has been expelled from the second chambers 408A, 408B, advancement of the movable members 404A, 404B towards the first end caps 412A, 412B creates a vacuum in the second chambers 408A, 408B that balances the vacuum in the first chambers 406A, 406B. Alternatively, the devices 401A, 401B can be shipped with the syringes 20A, 20B prefilled and the first and second chambers 406A, 406B and 408A, 408B "preprimed". Likewise, the devices 401A, 401B can alternatively be shipped with the first and second chambers 406A, 406B and 408A, 408B "preprimed" and a prefilled syringe installed on location.

Once the movable members 404A, 404B have been drawn rearward, the valves 432A, 432B are opened to allow atmospheric pressure to enter the second chambers 408A, 408B. While the actuator 50 is in an "off" state, fluid cannot be injected through the syringe outlets 30A, 30B and the movable members 404A, 404B cannot move forward within the first and second chambers 406A, 406B and 408A, 408B. This state is illustrated in FIG. 17.

After the fluid path set 403 is appropriately connected to the patient and the actuator 50 is placed in an "on" state, atmospheric pressure forces the movable member 404A of the first injection device 401A to move forward. The force created is transferred from plunger rod 418A and, thus, to plunger 25A, thereby forcing pressurized fluid through syringe outlet 30A to be injected into the patient through the fluid path set 403. This state is shown in FIG. 18. The one-way check valve 405 prevents the fluid from the first syringe 20A from being injected into the second syringe 20B because the fluid in the first syringe 20A is being injected at a higher pressure since the first syringe 20A has a smaller diameter than the second syringe 20B. Once the fluid within the first syringe 20A has been completely injected, the fluid within the second syringe 20B is injected. This state is shown in FIG. 19. In this manner, contrast or stress agent from the first syringe can be delivered to a patient followed by a saline flush.

Furthermore, it may be desirable to provide a two-phase contrast delivery followed by a saline flush. This could be accomplished using either fluid delivery system 300 or fluid delivery system 400 and providing releasable stops (not shown) that engage the plunger rods 318A, 318B, 418A, and/or 418B. Such stops would be controlled by the controller 70 and would allow the system to deliver a certain dose of contrast, followed by a saline flush, and then another dose of contrast.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A fluid delivery system comprising:
    a first injection device comprising:
        a first syringe configured to hold a first fluid and defining an outlet through which the first fluid can exit therefrom, the first syringe having a plunger slidably disposed therein and being configured to be placed in fluid connection with a patient; and
        a first pressurizing mechanism comprising a first vacuum drive in operative connection with the plunger of the first syringe for pressurizing the first fluid therein;
    a second injection device comprising:
        a second syringe configured to hold a second fluid and defining an outlet through which the second fluid can exit therefrom, the second syringe having a plunger slidably disposed therein and being configured to be placed in fluid connection with the patient; and
        a second pressurizing mechanism comprising a second vacuum drive in operative connection with the plunger of the second syringe for pressurizing the second fluid therein;
    a fluid path set extending from the outlet of the first syringe and the outlet of the second syringe to the patient;
    an actuator connected to the outlet of the first syringe and the outlet of the second syringe, the actuator being switchable between a first state in which the first fluid is prevented from flowing through the outlet of the first syringe and the second fluid is prevented from flowing through the outlet of the second syringe and a second state in which the first fluid can flow through the outlet of the first syringe and the second fluid can flow through the outlet of the second syringe;
    a controller provided remotely from the actuator and configured to control the actuator; and
    at least one one-way check valve positioned within the fluid path set,
    wherein the at least one one-way check valve is positioned within the fluid path set such that, upon switching the actuator by the controller, the at least one one-way check valve prevents the second fluid within the second syringe from being delivered until after the first fluid within the first syringe is delivered.

2. The fluid delivery system of claim 1, wherein the controller controls the actuator via ultrasound, via a protocol of an imaging scanner, via microwave energy, via a mechanical link, via infrared light, via fiber optic cable, via pneumatic power, via hydraulic power, via voice activation, via movement of a scanner table, via time delay, via an RF gradient trigger from a scanner, via a photo cell, via optical light, via an RF signal, or via line power.

3. The fluid delivery system of claim 1, wherein the at least one one-way check valve is positioned within the fluid path set downstream from the outlet of the second syringe and upstream from the outlet of the first syringe and the patient, and
    wherein a diameter of the first syringe is smaller than a diameter of the second syringe such that the first fluid within the first syringe is delivered at a higher pressure than the second fluid in the second syringe and the at least one one-way check valve prevents the first fluid from being delivered to the second syringe.

4. The fluid delivery system of claim 3, wherein the first fluid is different than the second fluid.

5. The fluid delivery system of claim 1, wherein the at least one one-way check valve comprises a first one-way check valve positioned within the fluid path set at the outlet of the first syringe and a second one-way check valve positioned within the fluid path set at the outlet of the second syringe, and
    wherein the second one-way check valve has a crack pressure that is greater than a crack pressure of the first one-way check valve such that, upon switching the actuator, the first fluid within the first syringe is delivered before the second fluid within the second syringe.

6. The fluid delivery system of claim 5, wherein the first fluid is different than the second fluid.

* * * * *